United States Patent
Tsuang et al.

(10) Patent No.: US 8,784,424 B2
(45) Date of Patent: Jul. 22, 2014

(54) MINIMALLY INVASIVE SPINAL STABILIZATION SYSTEM

(75) Inventors: Yang-Hwei Tsuang, Taipei (TW); Chun-Jen Liao, Taipei (TW); Huang-Chien Liang, Hsinchu (TW); Shih-Jui Han, Taichung (TW); Fon-Yih Tsuang, Taipei (TW); Chang-Jung Chiang, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 171 days.

(21) Appl. No.: 13/161,686

(22) Filed: Jun. 16, 2011

(65) Prior Publication Data

US 2012/0323278 A1    Dec. 20, 2012

(51) Int. Cl.
*A61B 17/70*    (2006.01)

(52) U.S. Cl.
USPC ........................................ 606/86 A

(58) Field of Classification Search
USPC ....... 606/139, 144, 146, 246, 264–279, 86 A, 606/103, 148, 153, 232
See application file for complete search history.

(56) References Cited

U.S. PATENT DOCUMENTS

| | | | | |
|---|---|---|---|---|
| 1,641,077 A * | 8/1927 | Fouquet | ................ | 140/121 |
| 4,312,337 A * | 1/1982 | Donohue | ................ | 606/80 |
| 5,728,112 A * | 3/1998 | Yoon | ................ | 606/144 |
| 5,730,747 A * | 3/1998 | Ek et al. | ................ | 606/148 |
| 5,908,428 A * | 6/1999 | Scirica et al. | ................ | 606/139 |
| 5,947,982 A * | 9/1999 | Duran | ................ | 606/139 |
| 6,051,006 A * | 4/2000 | Shluzas et al. | ................ | 606/148 |
| 6,086,596 A * | 7/2000 | Durham | ................ | 606/103 |
| 6,224,596 B1 | 5/2001 | Jackson | | |
| 7,008,422 B2 | 3/2006 | Foley et al. | | |
| 7,008,424 B2 * | 3/2006 | Teitelbaum | ................ | 606/262 |
| 7,108,705 B2 | 9/2006 | Davison et al. | | |
| 7,250,052 B2 | 7/2007 | Landry et al. | | |
| 7,824,410 B2 * | 11/2010 | Simonson et al. | ................ | 606/86 A |
| 7,892,238 B2 * | 2/2011 | DiPoto et al. | ................ | 606/86 A |
| 2003/0149431 A1 * | 8/2003 | Varieur | ................ | 606/61 |
| 2005/0154389 A1 | 7/2005 | Selover et al. | | |
| 2005/0273101 A1 | 12/2005 | Schumacher | | |
| 2006/0036252 A1 * | 2/2006 | Baynham et al. | ................ | 606/73 |
| 2007/0078460 A1 | 4/2007 | Frigg et al. | | |
| 2007/0270822 A1 * | 11/2007 | Heinz | ................ | 606/61 |
| 2008/0015584 A1 * | 1/2008 | Richelsoph | ................ | 606/61 |
| 2008/0114403 A1 * | 5/2008 | Kuester et al. | ................ | 606/308 |
| 2008/0234759 A1 * | 9/2008 | Marino | ................ | 606/309 |
| 2008/0312704 A1 * | 12/2008 | Hestad et al. | ................ | 606/86 A |
| 2009/0082809 A1 | 3/2009 | Nguyen et al. | | |
| 2009/0138029 A1 * | 5/2009 | Saliman et al. | ................ | 606/144 |
| 2009/0171392 A1 | 7/2009 | Garcia-Bengochea et al. | ................ | 606/246 |
| 2009/0221878 A1 | 9/2009 | Gorek | | |
| 2011/0087293 A1 | 4/2011 | Ferreira et al. | | |
| 2011/0184475 A1 | 7/2011 | Garcia-Bengochea et al. | | |

\* cited by examiner

*Primary Examiner* — Jan Christopher Merene
*Assistant Examiner* — Steven Cotroneo
(74) *Attorney, Agent, or Firm* — Cesari and McKenna, LLP

(57) ABSTRACT

A spinal fixation assembly includes a pedicle rod and pedicle screws which secure the pedicle rod to the spine. Each pedicle screw includes a head configured to receive a portion of the pedicle rod, and a threaded portion extending from a first end of the head and configured to engage a vertebra. The pedicle rod is secured to the head by a fastener. The head includes a breakaway region that defines a location in which at least a first portion of the head can be easily separated from the remainder of the head upon application of sufficient force to the first portion. A minimally invasive method of implanting the spinal fixation assembly is disclosed.

8 Claims, 23 Drawing Sheets

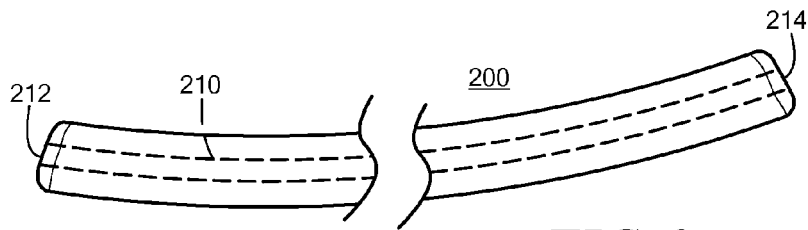
FIG. 3
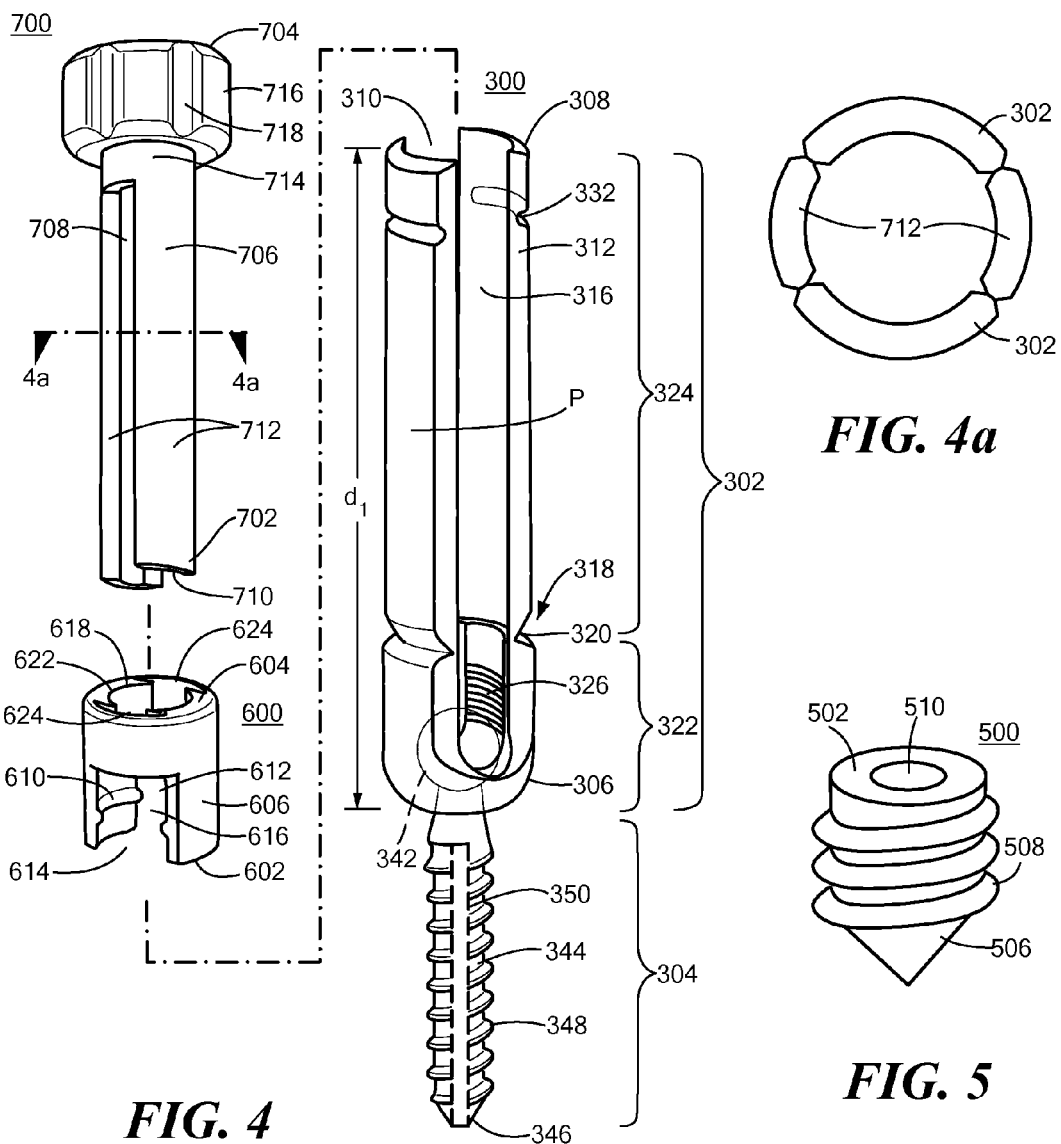
FIG. 4a
FIG. 4
FIG. 5

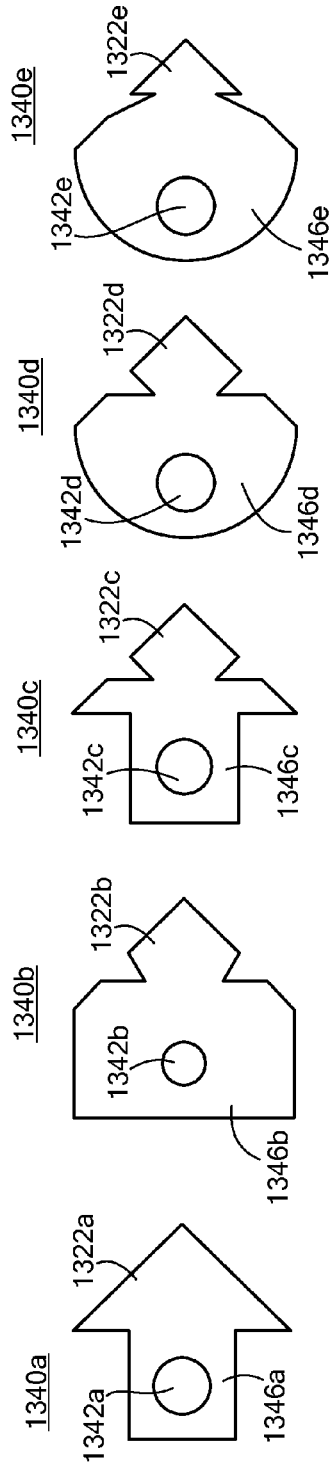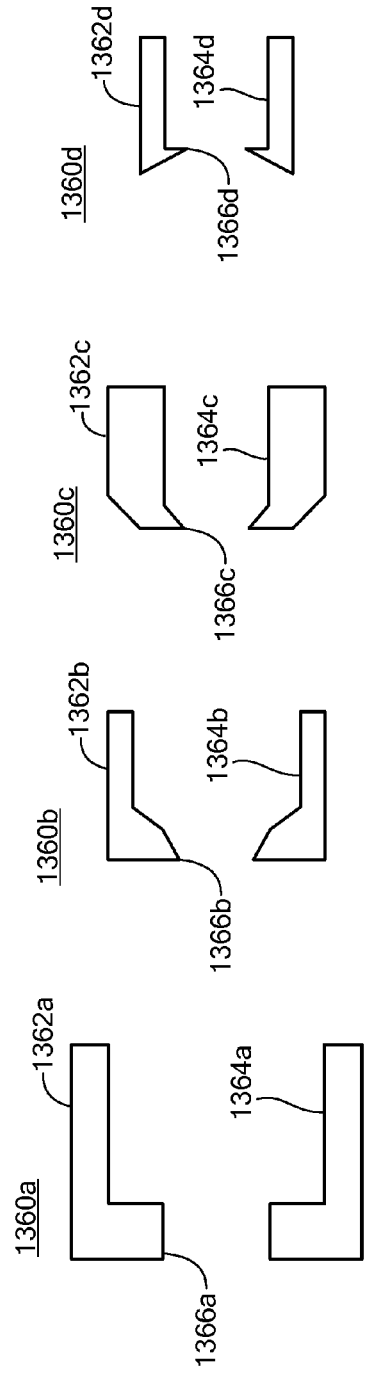

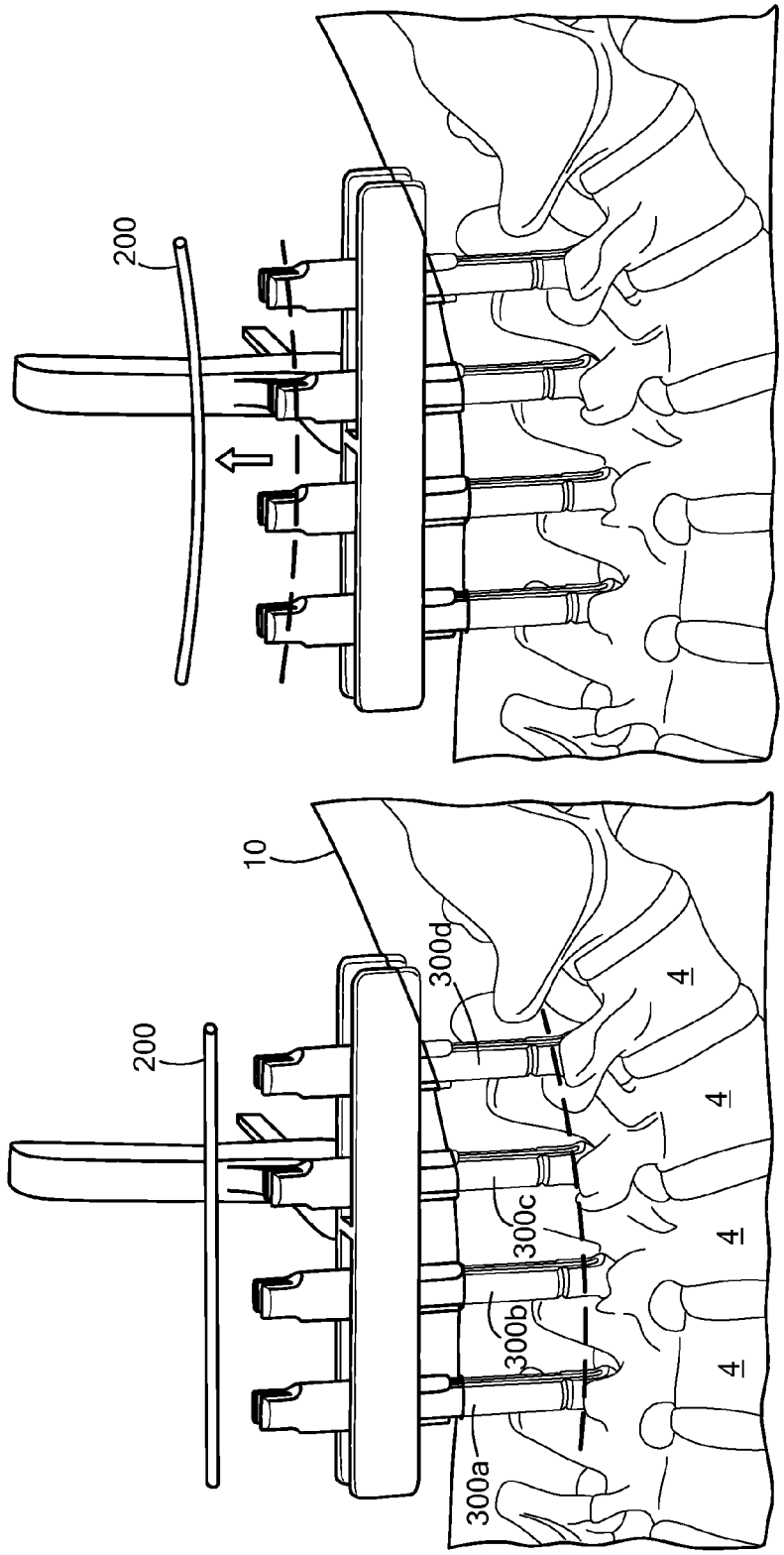

MINIMALLY INVASIVE SPINAL STABILIZATION SYSTEM

BACKGROUND

Each year 13 million people see a doctor for chronic back pain, which is estimated to cause 2.4 million Americans to be chronically disabled. About 25 percent of people who have back pain have a herniated disk. In the US, about 450 cases of herniated disk per 100,000 require surgery such as a discectomy.

Referring to FIG. 1, a discectomy (FIG. 1(a)) is performed when the intervertebral disc 8 has herniated or torn and has not responded to a more conservative treatment. When a surgeon performs a discectomy, it is usually performed through an incision in the patient's back at a location corresponding to the problem area of the spine 2. Muscles and ligaments are moved aside to expose the offending disc 8. The surgeon then uses a variety of surgical instruments to first separate the vertebrae 4 sandwiching the disc 8, and then remove the disc 8 completely. After a discectomy is performed, the spinal column at the operation site is separated to approximate the height of the removed disc (FIG. 1b), and then an artificial disk may be placed in the separation. Spinal fixation devices (FIG. 1(c)) are used to stabilize and/or align the spine 2 during the healing process following such procedures. In some cases, clinicians fill the separation with the implantation of autologous bone to achieve fusion (fusion is illustrated in FIG. 1(d)) to restore stability of the spine 2. Alternatively, discectomy may be followed by spinal fusion, or other procedure that may be deemed necessary to strengthen and straighten the spinal canal.

Although a discectomy is frequently performed using minimally invasive devices and procedures, it is still challenging to provide the minimally invasive spine stabilization that is required following this and other spinal procedures. Improved minimally invasive spinal fixation devices and methods are required to minimizing patient risk, trauma, recovery time, and to reduce the overall costs of such procedures.

SUMMARY

In some aspects, a minimally invasive spinal fixation assembly is provided. The minimally invasive spinal fixation assembly is configured to provide relative fixation of a series of vertebrae, and includes a pedicle rod and pedicle screws, each screw including a head configured to receive a portion of the pedicle rod, and a threaded portion extending from a first end of the head and configured to engage one of the vertebrae. The assembly further includes a fastener including external threads configured to engage corresponding threads formed on an inner surface of the head. The pedicle rod is secured to the head by the fastener, and the head includes a breakaway region. The breakaway region includes a portion of the head that is formed to be relatively structurally weak compared to the remaining portions of the head so as to define a location in which at least a first portion of the head can be easily separated from the remainder of the head upon application of sufficient force to the first portion.

The minimally invasive spinal fixation assembly may include one or more of the following features: The pedicle rod is configured to engage a suture. The pedicle rod is a hollow tube. Each pedicle screw includes the first end, and an open second end opposed to the first end. The head is generally tubular, and is formed of a single piece having a first opening that extends from the second end along an axial direction of the head to a location adjacent to, and spaced apart from, the first end, and a second opening on an opposed side of the body relative to the first opening, the second opening extending from the second end along an axial direction of the body to a location adjacent to and spaced apart from the first end. The first and second openings are diametrically aligned so as to form a transverse through channel through the head. A cap may be included that is configured to engage the second end of the pedicle screw head. The cap includes a hollow cylindrical body having an open end dimensioned to receive therein a second end of the head, and an opposed end, the opposed end including a central cap opening. The first end of the cap includes an interior surface having an annular protrusion, and the head includes a circumferential groove adjacent to the second end configured to engage the annular protrusion whereby the cap can be releasably secured to the second end of the head.

The minimally invasive spinal fixation assembly may include one or more of the following additional features: A U-shaped pedicle screw stabilizer may be included. The stabilizer includes a grip portion, an annular base extending from one side of the grip portion and having a diameter substantially equal to the diameter of the head, and a pair of legs extending from one side of the annular base, the legs configured to conform to the shape of, and be received within, the respective first and second openings of the of the head. A cap may be included that is configured to close the second end of the pedicle screw head and including a cap opening through which the legs of pedicle screw stabilizer can be received. A portion of the edge of the cap corresponding to the cap opening is formed having a shape that conforms to a cross sectional shape of a leg. The minimally invasive spinal fixation assembly further includes a pedicle screw breaking device configured to be received within an interior space of the pedicle screw head and facilitate separation of the second end of the head from the first end of the head along a prescribed circumferential breakaway line provided on the head between the first and second ends of the head.

The minimally invasive spinal fixation assembly may include one or more of the following additional features: A suture guide assembly may be included. The suture guide assembly includes a suture leader configured to retain a suture, and a guide tool including pivotably-joined first and second arms. The first arm terminates at a first end in a male suture guide, and the second arm terminates at a first end in a female suture guide. The male and female suture guides are configured to permit the suture leader to be passed from the male suture guide to the female suture guide upon movement of the first and second arms between an open position in which the male and female suture guides are spaced apart and a closed position in which the male and female suture guides are adjacent. The suture leader comprises a tip shaped to facilitate insertion into the female suture guide, and an opening formed adjacent to the tip. The first and second arms are configured to be received within the hollow interior space of the pedicle screw head and pass through the first and second openings. The series of vertebrae includes at least two vertebrae. The spinal fixation assembly is configured to be implemented via non-continuous wound sites having a length generally corresponding to a cross sectional dimension of the head.

In some aspects, a pedicle screw for use in spinal fixation is provided. The pedicle screw includes a head including a first end, and an open second end opposed to the first end, and a threaded body extending from the first end. The head is tubular, and is formed of a single piece having a first opening that extends from the second end along an axial direction of the head to a location adjacent to, and spaced apart from, the first end, and a second opening on an opposed side of the body relative to the first opening, the second opening extending from the second end along an axial direction of the body to a location adjacent to and spaced apart from the first end. The first and second openings are diametrically aligned so as to form a transverse through channel through the head.

The pedicle screw may include one or more of the following features: The distance between first and second ends of the head is in a range from 40 mm to 120 mm. The distance between first and second ends of the head is in a range from 50 mm to 80 mm. The head includes breakaway region located between the first and second ends, the breakaway region including a portion of the head that is formed to be relatively structurally weak compared to the remaining portions of the head so as to define a location in which at least a portion of the second end can be easily separated from the head upon application of sufficient force to the second end. The breakaway region includes a circumferential groove positioned between the first end and a midpoint between the first and second ends, the circumferential groove configured to provide a prescribed breakaway line along which at least a portion of the second end can be easily separated from the head upon application of sufficient force to the second end. The force is a twisting force about a longitudinal axis of the head. The pedicle screw further includes a removable cap configured to close the head second end, wherein the head includes a circumferential groove adjacent to the second end configured to engage a corresponding annular lip provided on an interior surface of the cap. The first end of the head is configured to permit poly-axial rotation of the threaded body relative to the head.

In some aspects, a suture guide assembly is provided. The suture guide assembly includes a suture leader configured to retain a suture, and a guide tool including pivotably-joined first and second arms. The first arm terminates at a first end in a male suture guide, and the second arm terminates at a first end in a female suture guide. The male and female suture guides are configured to permit the suture leader to be passed from the male suture guide to the female suture guide upon movement of the first and second arms between an open position in which the male and female suture guides are spaced apart and a closed position in which the male and female suture guides are adjacent.

The suture guide assembly may include one or more of the following features: The suture leader includes a conical tip, and an eye protruding from the conical tip. The male suture guide includes a cylindrical stem configured to releasably engage the suture leader eye, and the female suture guide includes cylindrical shell configured to releasably engage the suture leader conical tip, and the guide tool is configured so as to support the male and female suture guides so that the conical tip at least partially received within the shell when the guide tool is in the closed position. The shell includes a first shell opening through which the suture leader is inserted into the shell, and a second shell opening through which the suture leader is withdrawn from the shell. The second shell opening has a shape that generally conforms to the shape of the suture leader. The first shell opening has a dimension that is smaller than the dimension of the widest portion of the suture leader. The suture leader includes a conical tip, and when the guide tool is moved from the open position to the closed position, the conical tip of the suture leader is driven through the first shell opening, and is prevented from being retracted from the shell via the first shell opening. The first and second arms are angled. The arm angle is between 90-180 degrees.

In some aspects, a minimally invasive method for achieving spinal stabilization is provided. The method includes the following method steps: Implanting a pedicle screw into each vertebra of a portion of the spine to be stabilized, each pedicle screw implanted through a unique incision. Subcutaneously threading a suture through a corresponding passage provided in each pedicle screw. Withdrawing a leading end of the suture from the body through an access incision. Subcutaneously threading a hollow pedicle rod through the passage of each pedicle screw by passing the pedicle rod along the suture through the access incision into the body and through each respective passage such that the pedicle rod spans all implanted pedicle screws. Securing the pedicle rod relative to each pedicle screw.

The method may include one or more of the following additional steps and/or features: At least two pedicle screws are implanted. The implanting step includes providing an incision through the skin overlying the vertebra, where the incision length generally corresponds to the outer diameter of the pedicle screw; forming a hole in the pedicle; inserting a Kirshner pin at the desired implantation location; dilating soft tissues in the vicinity of the Kirshner pin; implant the pedicle screw in the hole of the vertebra by passing it along the Kirshner pin and screwing the pedicle screw into the hole in the vertebra; and removing the Kirshner pin from the incision, leaving the pedicle screw in place. The step of threading a suture includes linking the pedicles screws by subcutaneously threading a suture through each respective pedicle screw head. The step of linking the pedicle screws includes the following: passing a suture through the interior space of the pedicel screw head from a second end of the pedicle screw head to a first end of the screw head along a longitudinal axis of the pedicle screw head, the first end being closer to the spine than the second end; guiding the suture from the first end of the pedicle screw in a direction generally parallel to a longitudinal axis of the spine to the first end of an adjacent pedicle screw; withdrawing the suture from the adjacent pedicle screw head; and repeating the passing and guiding steps for the adjacent pedicle screw and any remaining pedicle screws. Prior to the step of threading a hollow pedicle rod, the following step is performed: adjusting the curvature of the rod ex vivo and prior to insertion into the body by bending the rod to correspond to the curvature of a line defined by upper surfaces of the implanted pedicle screws. The securing step further comprises engaging exterior threads of a set screw with corresponding threads provided on an interior surface of the pedicle screw such that the pedicle rod is retained between the set screw and the surface the pedicle screw. The pedicle screw includes a head including a first end, and a second end opposed to the first end, a threaded body extending from the first end, and an annular breakaway region located between the first and second ends. The breakaway region includes a portion of the head that is formed to be relatively structurally weak compared to the remaining portions of the head so as to define a location in which at least a portion of the second end can be easily separated from the head upon application of sufficient force to the second end. The securing step further comprises engaging exterior threads of a set screw with corresponding threads provided on an interior surface of the pedicle screw head such that the pedicle rod is retained on the interior surface of the pedicle screw head at a location between the first end and the breakaway region. The method further comprises the steps of removing a portion of the pedicle screw by applying a force to the portion such that the portion breaks away from the remainder of the pedicle screw along a predetermined breakaway line. The force is a twisting force or a compressive force. The hollow pedicle rod is at least 10 cm in length, and is inserted into the body through the access incision of up to about 1 cm in length. Each pedicle screw is implanted through a unique incision of up to about 1 cm in length.

The minimally invasive spinal fixation device described herein can be implanted through a series of small incisions of about 1 cm or less along the region of the spine to be supported. Advantageously, this device avoids several drawbacks associated with many conventional spinal fixation devices. In particular, the minimally invasive spinal fixation device described herein does not need a large incision of 10 cm or more through which a spinal fixation cage can be implanted. As a result, patient risks of blood loss, infection, and/or tissue damage which can lead to lower back weakness can be avoided. In addition, recovery time and negative side effects are minimized.

The spinal fixation device includes pedicle screws that secure a pedicle rod to the respective vertebra within the region of the spine to be stabilized. Each pedicle screw includes a U-shaped head and a threaded portion that extends from one end of the head. The head is formed of an elongated single body having a circumferentially-extending, annular breakaway region. In fact, the pedicle screw head has a sufficient length to protrude upward out of the incision so as to permit manipulation during implantation, and after implantation is complete, the excess length of the pedicle screw head can be broken off along the pre-defined breakaway region. Since the pedicle screw head is manufactured as a single body, no preassembly of the screw head is required prior to implantation as is required in some conventional pedicle screws, and there is no risk of malfunction or loss of small components into the wound site during implantation. Due to the fact that the pedicle screw head includes the breakaway region, removal of the excess portions of the head after implementation is a very simple and quick procedure.

The method of implanting the spinal fixation device employs a novel method of threading a suture through a series of implanted pedicle screws, and then using the suture to link the pedicle screws using a pedicle rod. This method is advantageous since it can be accomplished performed subcutaneously and submuscularly via minimal incisions. Moreover, the disclosed method permits a larger region of the spine to be fixed than some known minimally invasive spinal fixation methods. For example, the method permits a series of four or more adjacent vertebra to be fixed.

Modes for carrying out the present invention are explained below by reference to an embodiment of the present invention shown in the attached drawings. The above-mentioned object, other objects, characteristics and advantages of the present invention will become apparent from the detailed description of the embodiment of the invention presented below in conjunction with the attached drawings.

BRIEF DESCRIPTION OF THE DRAWINGS

FIG. 3 is a side view of a pedicle rod used in the spinal fixation system of FIG. 2.

FIG. 4 is an exploded perspective view of a pedicle screw assembly including a pedicle screw as used in the spinal fixation system of FIG. 2, a cap and a stabilizer tool.

FIG. 4a is a cross-sectional view of the pedicle screw assembly of FIG. 4, as seen across line 4a-4a.

FIG. 5 is a perspective view of a fastener used in the spinal fixation system of FIG. 2.

FIG. 6b is an enlarged view of the portion of the breaking tool marked as 6b in FIG. 6a.

FIG. 8(a)-8(e) are alternative embodiments of a male suture guide of the guide tool assembly of FIG. 7.

FIG. 9(a)-9(d) are alternative embodiments of a female suture guide of the guide tool assembly of FIG. 7.

FIGS. 30-31 illustrate using the exposed ends of the pedicle screws as a template for preshaping the pedicle screw rod to the shape of the spine prior to implantation.

DETAILED DESCRIPTION

Figure 1A:
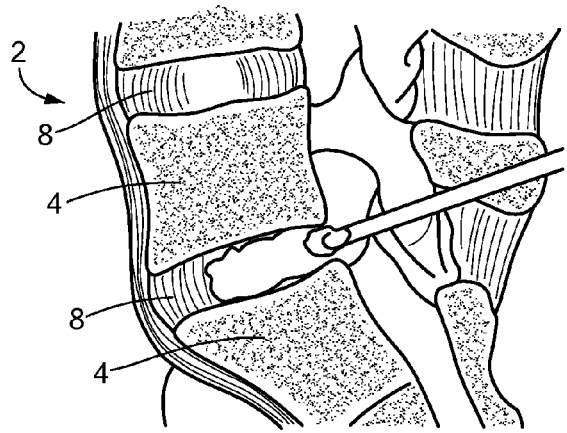
FIGS. 1 (a)-1(d) illustrate procedures for repairing a herniated disk.
Figure 1B:
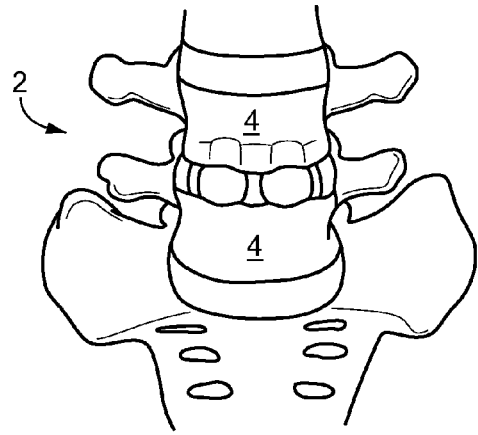
Figure 1C:
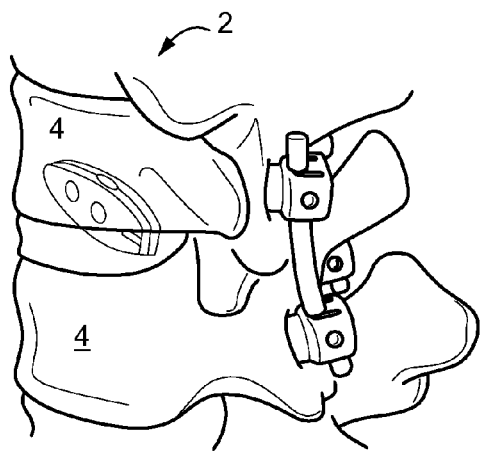
Figure 1D:
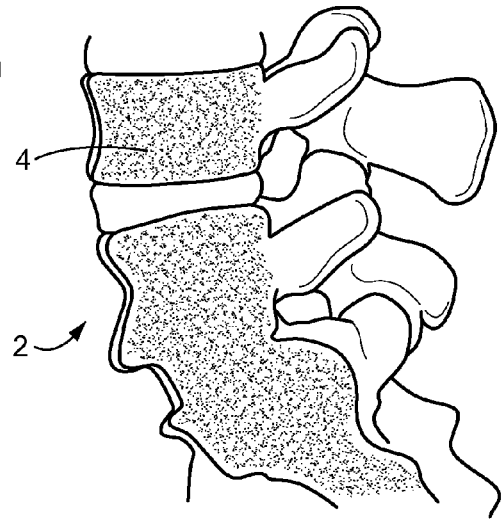
Figure 2:
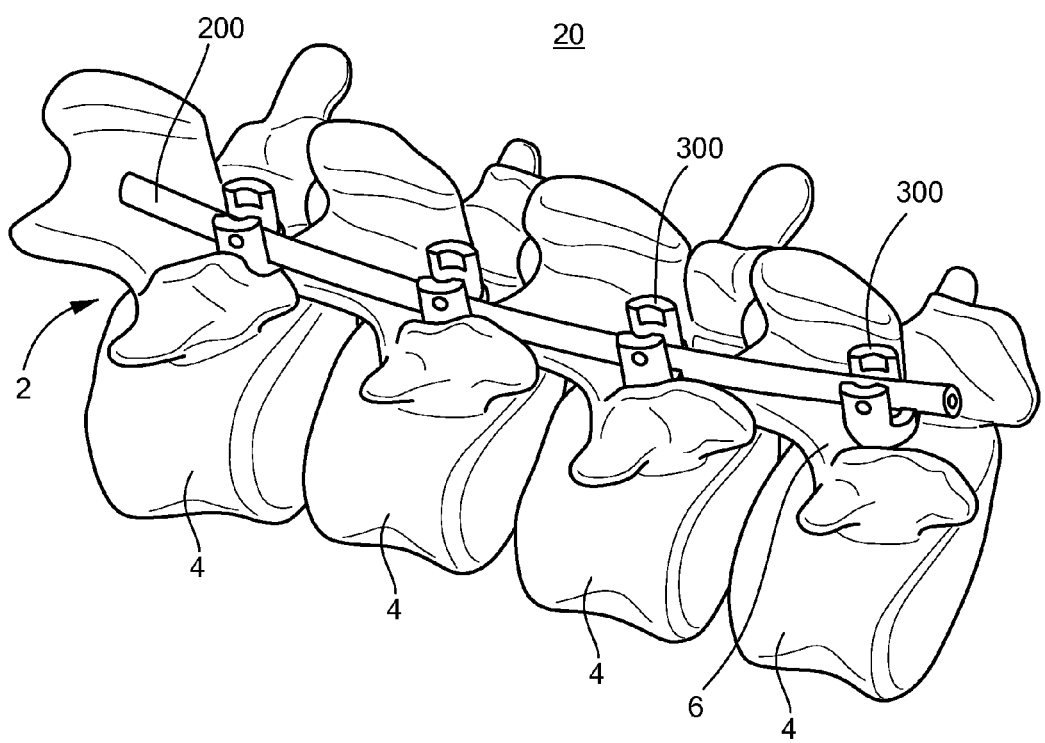
FIG. 2 is a perspective view of a minimally invasive spinal fixation system implanted on a series of four adjacent vertebrae.

Referring to FIG. 2, a minimally invasive spinal fixation system 20 used to stabilize a region of the spine 2 includes a fixation rod 200 of sufficient length to extend across the vertebrae 4 to be stabilized, pedicle screws 300 for anchoring the fixation rod 200 to each corresponding vertebra 4, and a fastener 500 on each pedicle screw 300 to secure the pedicle rod 200 to the pedicle screw 300. Each pedicle screw 300 is implanted in the pedicle 6 of the corresponding vertebra 4 through a small skin incision having a length generally corresponding to a cross sectional dimension of the pedicle screw 300. In the illustrated embodiment, for example, the incision has a length of 1 cm or less, and the rod 200 is assembled with the pedicle screws 300 through a separate skin incision of 1 cm or less, as discussed further below.

Referring to FIG. 3, the fixation rod 200 is a structure that is configured to engage a suture, where a suture is defined herein as an elongated strand or fiber such as a thread or wire. In the illustrated embodiment, the fixation rod 200 is a hollow tube, including a first end 212, a second end 214 that is opposed to the first end 212, and an interior passageway 210 that extends between the first end 212 and the second end 214. In this embodiment, the fixation rod 200 can receive a suture within the passageway 210.

The rod 200 is relatively long compared to its cross-sectional dimension. For example, in the illustrated embodiment, the rod 200 is cylindrical, and it has a diameter of 5.5 mm and an axial length that corresponds to the overall length of the region of the spine 2 to be stabilized. For example, to stabilize two adjacent vertebrae 4, the rod has a length of approximately 60.0 mm. To stabilize a series of four adjacent vertebrae 4, the rod has a length of approximately 150.0 mm. The rod 200 is formed of an implantable material, and is formed of a material of sufficient strength and stiffness to provide spinal stabilization, while also being sufficiently malleable to permit shaping of the rod curvature. For example, the rod 200 may be formed of a titanium alloy such as Ti6Al4V.

Referring to FIG. 4, a polyaxial pedicle screw 300 is used to anchor the pedicle rod 200 to each corresponding vertebra 4. Each pedicle screw 300 is dimensioned to be inserted through a skin incision of 1 cm or less and screwed into the pedicle of the corresponding vertebra 4, which lies below the skin and underlying muscle at a depth of about 5 cm for an average male. Toward this end, each pedicle screw 300 includes an elongated head 302 and a threaded tip 304.

The head 302 is generally tubular, and is formed of a single piece. The head 302 includes a closed first end 306, and an open second end 308 that is opposed to the first end 306. The head 302 is provided with a first axially-extending opening 310 that extends from the second end 308 to a location adjacent to, and spaced apart from, the first end 306. The head 302 is also provided with a second axially-extending opening 312 on an opposed side of the head 302 relative to the first opening 310. Mirroring the first opening 310, the second opening 312 extends from the second end 308 to a location adjacent to and spaced apart from the first end 306. The first and second openings 310, 312 are diametrically aligned so as to form a transverse through channel 316 through the head 302. As a result, the head 302 is generally U shaped.

The head 302 is long in an axial direction relative to its cross sectional dimension. For example, in the illustrated embodiment, the distance d1 between the first end 306 and the second end 308 is in a range from 4 cm to 12 cm, whereas it has a diameter of about 1 cm. In other embodiments, the distance d1 may be in a range of 5 cm to 8 cm.

The head 302 is provided with an annular breakaway region 318 that is located between the first end 306 and the second end 308. In the illustrated embodiment, the breakaway region 318 is located between the first end 306 and a midpoint P between the first and second ends 306, 308, or more specifically, at a location about midway between the point P and the first end 306. As a result, the head 302 is partitioned into two portions by the breakaway region 318. A ventral portion 322 that extends between the first end 306 and the breakaway region 318; and a dorsal portion 324 that extends between the breakaway region 318 and the second end 308. The breakaway region 318 is a region of the head 302 that is formed to be relatively structurally weak compared to the remainder of the head 302 so as to define a circumferential line along which the dorsal portion 324 can be easily separated from the ventral portion 322 upon application of sufficient force to the dorsal portion 324. In the illustrated embodiment, the breakaway region 318 is a circumferentially-extending V-shaped groove 320. In some embodiments, the spinal fixation system 20 may include a screw breaking tool 800, described further below, that is configured to provide a twisting force about a longitudinal axis of the head 302 and thereby selectively separate the dorsal portion 324 from the ventral portion 322 at the groove 320. It will be appreciated that although a bending force could also be applied to the dorsal portion 324 to achieve separation, use of a twisting force will be less damaging to surrounding tissues than a bending force.

The interior surface of the ventral portion 322 is provided with threads 326 configured to engage corresponding threads 508 provided on an outer surface 506 of a fastener 500, described further below. In addition, a retention groove 332 is formed in the outer surface of the head 302 at a location adjacent the second end 308. The retention groove 332 is dimensioned and positioned so as to receive and retain a corresponding annular ridge 610 formed on an inner surface of a screw cap 600, described further below.

The threaded tip 304 of the pedicle screw 300 extends outward from the first end 306 of the head 302. More specifically, the threaded tip 304 includes a base 342 that is supported within the first end 306 of the head 302, and a shank 344 that extends from the base. The first end 306 of the head 302 is configured to permit three dimensional rotation of the threaded tip 304 relative to the head 302. The shank 344 has outer threads and terminates at an apex 346. In addition, the threaded tip 304 includes an axial through hole 350 that opens at the base 342, extends through the shank 344 and opens the apex 346.

Referring to FIG. 5, the fastener 500 is a cylindrical member having external threads 508 formed on an outer surface 506. The threads 508 are configured to engage corresponding threads 326 formed on an inner surface of the ventral portion 322 of the pedicle screw head 302. In the illustrated embodiment, the fastener 500 is a set screw having a first end 502 that is configured to receive a driving tool. For example, the end 502 includes a hexagonal-shaped socket 510 suited for receiving a hex wrench, or the shaped tip 892 of an actuator tool 850 (described below). In use, the fastener 500 is secured to the ventral portion 322 of the pedicle screw head 302 so as to retain the position of the fixation rod 200 relative to the pedicle screw 300.

Referring again to FIG. 4, the spinal fixation system 20 further includes a removable screw cap 600 that is shaped and dimensioned to be secured to the pedicle screw head second end 308, to support and stabilize the head second end 308, and to serve as a guide to direct a stabilizer tool 700 (described below) during insertion of the stabilizer tool 700 into the hollow interior of the pedicle screw 300 (described below). The screw cap 600 is a hollow cylinder having an open first end 602, a closed second end 604 opposed to the first end 602, and a sidewall 606 extending between the first end 602 and the second end 604. The open first end 602 is dimensioned to receive the second end 308 of the pedicle screw head 302 therein.

The screw cap sidewall 606 is provided with a first axially-extending cap opening 612 that extends from the first end 602 to a location adjacent to, and spaced apart from, the second end 604. The screw cap sidewall 606 is also provided with a second axially-extending cap opening 614 on an opposed side of the sidewall 606 relative to the first cap opening 612. Mirroring the first cap opening 612, the second cap opening 614 extends from the first end 602 to a location adjacent to and spaced apart from the second end 604. The first and second cap openings 612, 614 are diametrically aligned so as to form a transverse through channel 616 through the screw cap 600. When the screw cap 600 is disposed on the second end 308 of the pedicle screw head 302, the screw cap transverse through channel 616 can be aligned with the pedicle screw through channel 316.

The screw cap 600 includes an inwardly-protruding annular ridge 610 formed on an interior surface of the sidewall 606 that is sized and positioned to permit engagement with the cap retention groove 332 formed on the pedicle screw second end 608. The protruding ridge 610 extends about the inner circumference of the sidewall, and cooperates with the retention groove 332 to maintain the screw cap 600 on the pedicle screw second end 308.

In addition, the second end 604 of the screw cap 600 includes a central opening 618. The central opening 618 has an irregular shape, including a generally circular central portion 622 and an elongated portion 624 positioned along each opposed side of, and intersecting, the central portion 622. In the illustrated embodiment, the central portion 622 is shaped and dimensioned to permit passage of surgical tools through the screw cap 600 and into the interior space of the pedicle screw head 302. In addition, the elongated portions 624 are shaped and dimensioned to receive leg portions 712 of the stabilizer tool 700 when the stabilizer tool 700 is inserted into the hollow interior of the pedicle screw 300 (described below). It should be noted that the elongated portions 624 of the central opening 618 are located along a periphery of the second end 604 so as to overlie respective first and second cap openings 612, 614. This configuration ensures that the leg portions 712 of the stabilizer tool 700 are aligned with respective first and second openings 310, 312 of the pedicle screw head 302 after assembly of the pedicle screw 300, cap 600 and stabilizer tool 700, as discussed further below.

The spinal fixation system 20 further includes the stabilizer tool 700 which is a hollow cylinder including an open first end 702, a closed second end 704 opposed to the first end 702, and a sidewall 706 extending between the first end 702 and the second end 704. The sidewall 706 is formed having an outer diameter that corresponds to that of the pedicle screw head 302 and diametrically opposed openings 708, 710 that extend axially from the first end 702 to a location adjacent the second end 704. The openings 708, 710 provide the sidewall 706 with a generally U-shape, including leg portions 712 that are joined by an annular base portion 714. A grip portion 716 is disposed between the base portion 714 and the second end 704 that has a larger outer diameter than the base portion 714, and includes surface features such as axially-extending grooves 718 to improve gripability. In addition, the second end 704 includes a central opening (not shown in FIG. 4) through which tools can be inserted.

When the stabilizer tool 700 is assembled with the cap 600 and pedicle screw 300, the leg portions 712 reside within the openings 310, 312 of the pedicle screw head 302 (see FIG. 4a). The stabilizer tool 700 is used to position the pedicle rod 200 within the interior space of the pedicle screw head 302 during implantation of the spinal fixation system 20. In addition, the stabilizer tool 700 is used to maintain the position of the pedicle rod 200 while the fastener 500 is used to secure the pedicle rod 200 to the ventral portion 322 of the pedicle screw head 302, and to reinforce the dorsal portion 324 during separation of the dorsal portion 324 from the ventral portion 322 after implantation, as discussed further below.

Figure 6A:
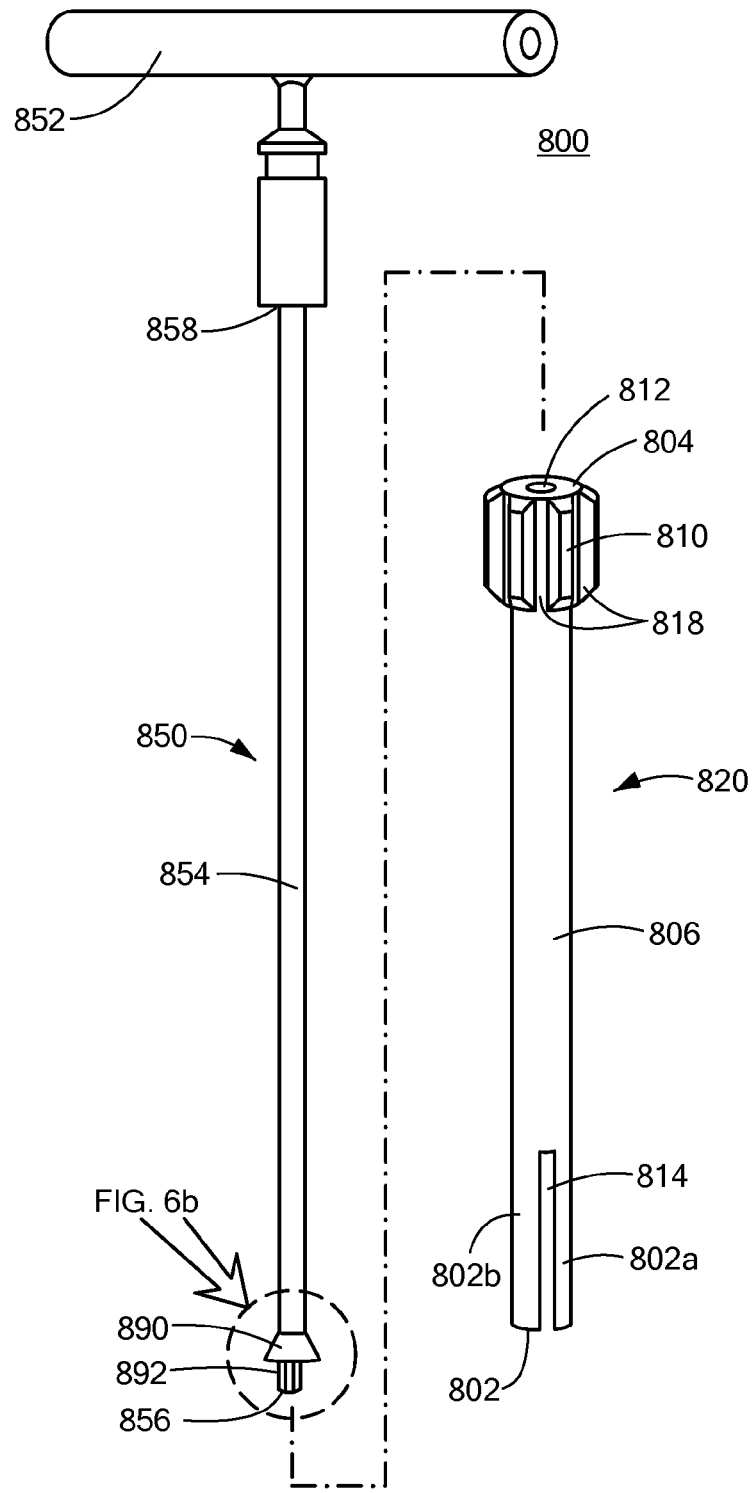
FIG. 6a is an exploded view of a breaking tool used during implantation of the spinal fixation system of FIG. 2.
Figure 6B:
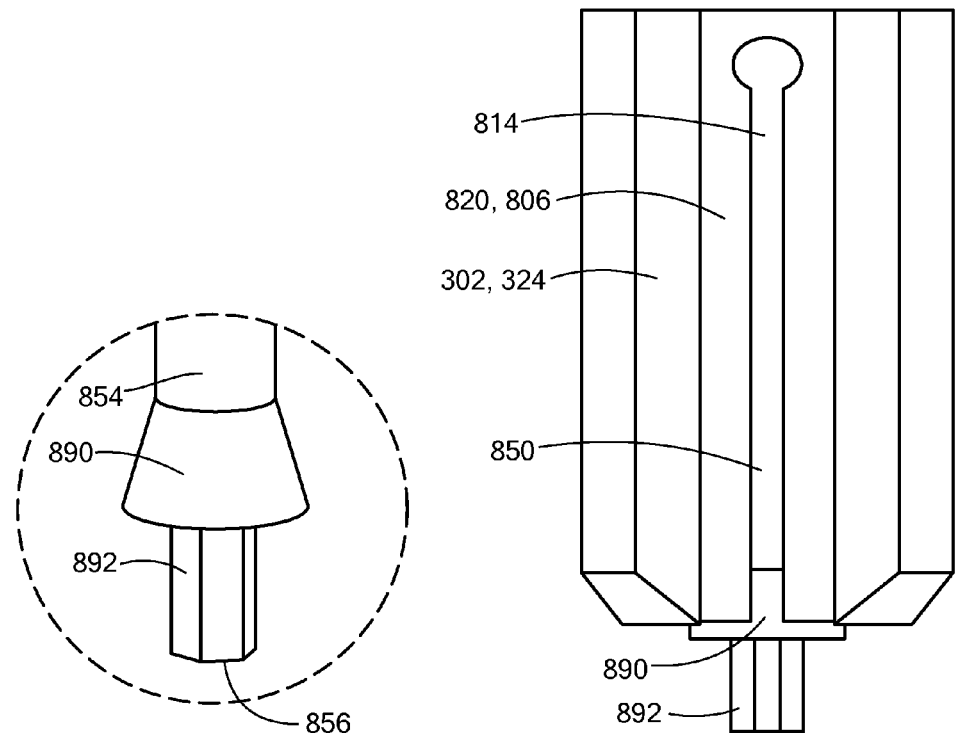
Figure 6C:
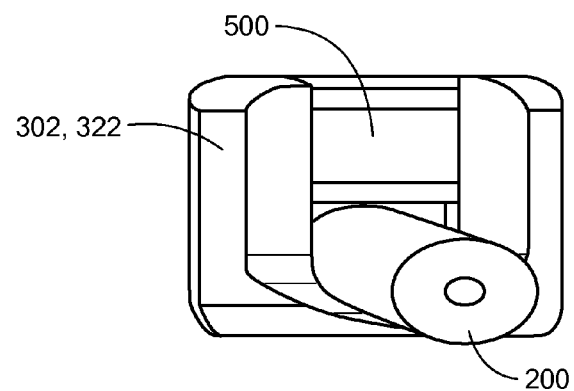
FIG. 6c illustrates the breaking tool in use separating the pedicle head into two portions.

Referring to FIGS. 6a-6c, the spinal fixation system 20 further includes the screw breaking tool 800 that is configured to be received within the interior space of the pedicle screw head 302 and is used to remove the dorsal portion 324 of the pedicle screw head 302 once the pedicle screw ventral portion 322 and pedicle rod 200 are correctly positioned and mutually fixed. The screw breaking tool is 800 includes a sleeve 820 and a T-shaped actuator 850 shaped and dimensioned to be received within the sleeve 820 (FIG. 6a). The sleeve 820 is a hollow cylinder that includes an open first end 802, a second end 804 opposed to the first end 802, and a sidewall 806 extending between the first end 802 and the second end 804. A pair of slots 814 (only one slot 814 is shown) extend from the first end 802 toward a mid portion of the sleeve 820. The slots 814 divided the first end 802 into two end portions 802a, 802b. A grip region 810 is provided on the second end 804 that has a larger outer diameter than the sidewall 806, and includes surface features such as axially-extending grooves 818 to improve gripability. In addition, the second end 804 includes a central opening 812 through which tools, including the actuator 850, can be inserted. The axial length of sleeve 820 is greater than that of an assembly of the pedicle screw 300, cap 600 and stabilizer tool 700.

The actuator 850 includes a shank 854 having a first end 856 and a second end 858. A handle 852 is fixed to the second end 858, giving the actuator its T-shape. The shank first end 856 includes a flared portion 890, and a shaped portion 892 that extends coaxially from the flared portion 890 (FIG. 6b). The shaped portion 892 has an outer cross sectional dimension that is less than that of the flared portion 890 and shank 854, and includes surface features that enable it to engage the socket 510 of the fastener 500. For example, in the illustrated embodiment, the shaped portion 892 is hexagonal in cross-sectional shape so as to engage the hexagonal socket 510 of the fastener 500. The flared portion 890 has an outer dimension that is greater than that of the sleeve sidewall 806 and the diameter of the interior space of the pedicle screw head 302. When the actuator 850 is assembled within the sleeve 820 with the flared portion 890 protruding beyond the sleeve first end 802, the sleeve 820 can be inserted into the screw head 302, for example to secure the fastener 500 to the screw head 302. By drawing the actuator 850 upward so that at least a portion of the flared portion 890 is disposed within first end of the sleeve 820, the flared portion 890 causes the two end portions 802a, 802b to slightly separate. By this action, the outer wall of the sleeve 820 is compressed against the inner wall of the pedicle screw head dorsal portion 324. Due to frictional engagement of the sleeve 820 with the pedicle screw head 302, by rotating the actuator 850 about its longitudinal axis, a twisting force is applied to the dorsal portion 324 of the screw head 302. Upon application of sufficient force, the dorsal portion 324 of the screw head 302 can be separated from the ventral portion 322 along the breakaway line 318 (FIG. 6c).

Figure 7:
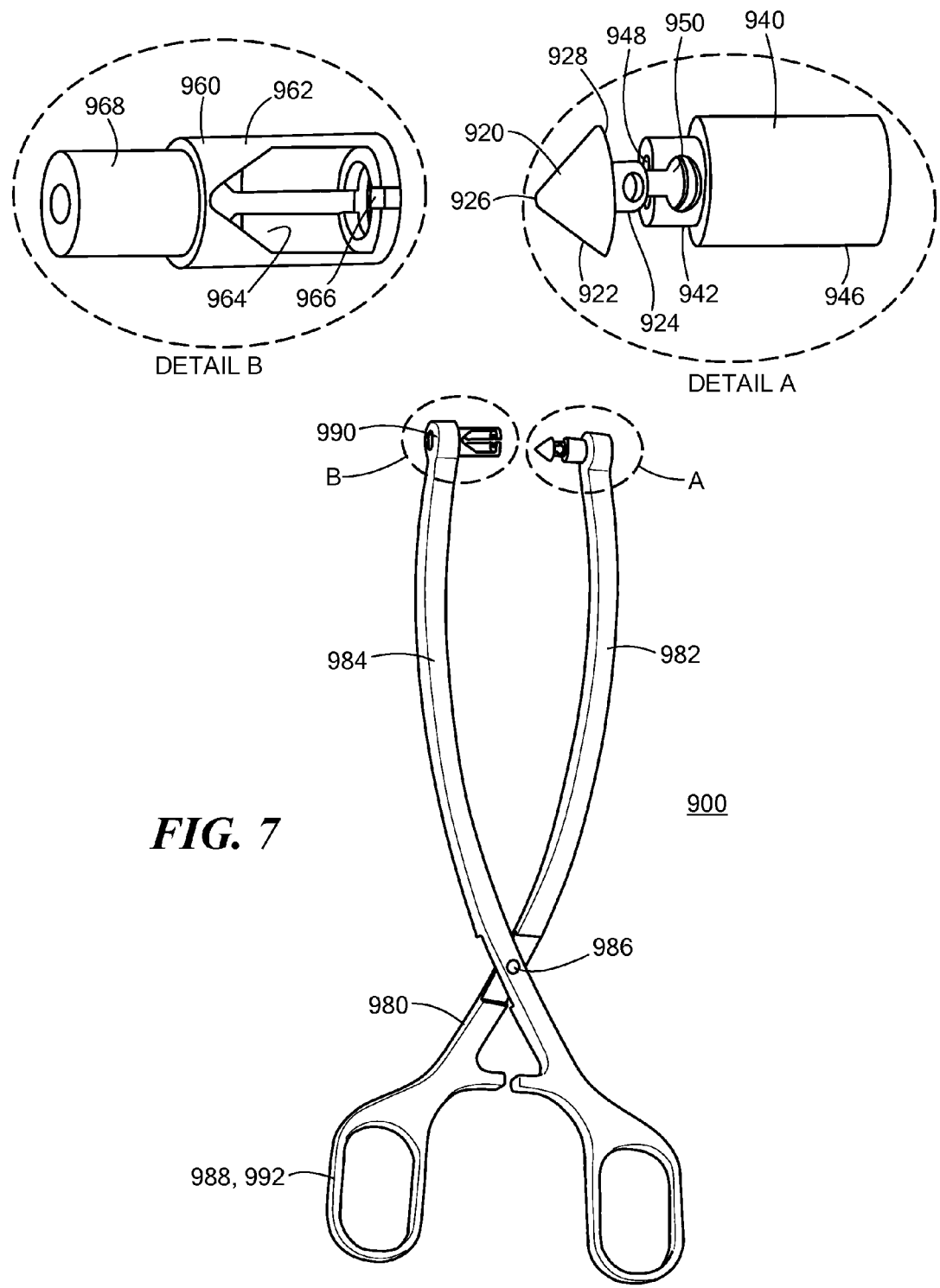
FIG. 7 is a perspective view of a guide tool assembly.

Referring to FIG. 7, a suture guide assembly 900 is used to implant the pedicle rod 200 within each respective pedicle screw head 302, as discussed further below. The suture guide assembly 900 includes a guide tool 980 having a pair of elongated arms 982, 984 that are joined via a pivot pin 986 at a location between respective arm first ends 988 and respective arm second ends 990. The first end 988 of each arm 982, 984 is formed into a finger loop 992 to permit manual actuation of the tool, and the second end 990 of each arm 982, 984 is configured to hold a suture guide 940, 960. During actuation, the arms 982, 984 of the guide tool 980 move in a scissoring motion about the pin 986.

Figure 39:
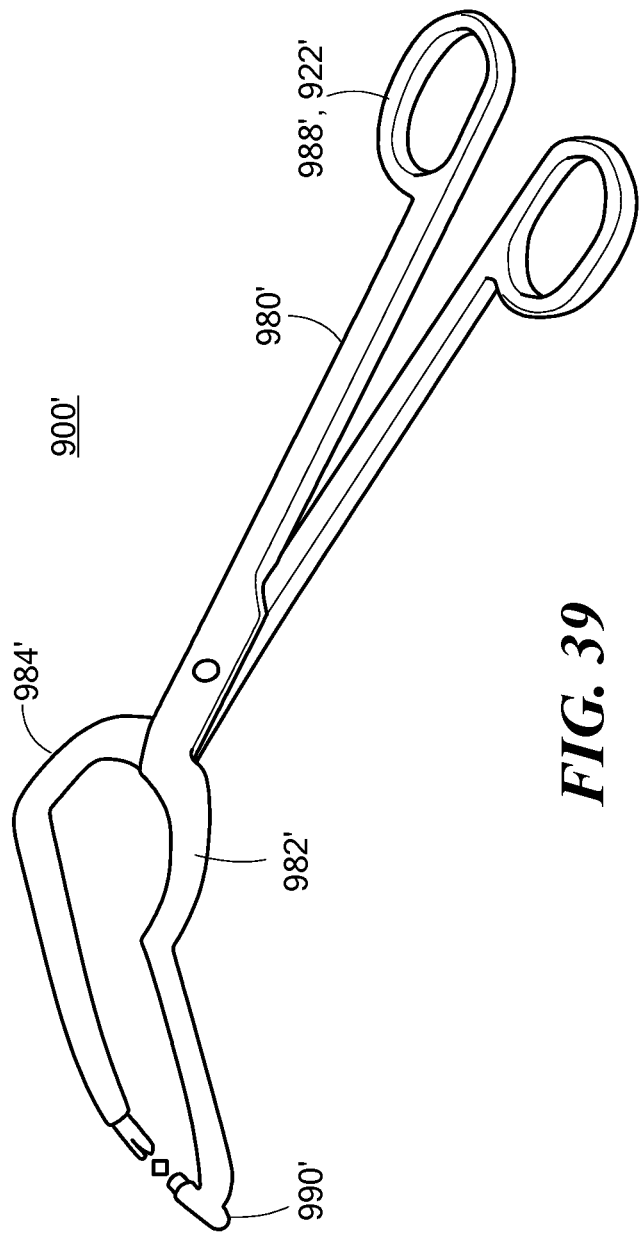
FIG. 39 is a perspective view of another embodiment of a guide tool assembly.

The first and second arms 982, 984 of the guide tool 980 are each dimensioned to be received within the hollow interior space of the pedicle screw head 302 and to extend along the axial length of the pedicle screw head 302. Moreover, the guide tool 980 operates in a scissoring motion in which the first arm 982 and the second arm 984 move between an open position (shown in FIGS. 7 and 22-23) in which the second ends 990 of the arms 982, 984 are spaced apart a first distance, and a closed position in which the second ends 990 of the arms 982, 984 are spaced apart a second distance (shown in FIG. 24), the first distance being greater than the second distance. The first and second arms 982, 984 are dimensioned to pass through the pedicle screw head first and second openings 310, 312 when the guide tool 980 is actuated while the guide tool 980 is inserted in a pedicle screw 300, as discussed further below. In some embodiments, the first and second arms 982', 984' can be angled. For example, the arms 982', 984' may be angled midway between the pivot pin 986' and the arms second ends 990', so that the second ends 990' lie out of a plane defined by the finger loops 992' (FIG. 39). The arm angle may be in a range between 90-180 degrees.

The suture guide assembly 900 also includes a leader 920 that retains an end of a suture 1216 (not shown in FIG. 7), a male suture guide 940 mounted on the first arm 982 of the guide tool 980, and a female suture guide 960 mounted on the second arm 984 of the guide tool 980.

Referring to FIG. 7, detail A, the leader 920 includes a conical tip 922 having an apex 926. In addition, the leader 920 includes an eyelet 924 protruding from the tip 922 on a side 928 opposite to the apex 926. The diameter of the eyelet 924 is small relative to the diameter of the side 928. In use, a suture 1216 is secured to the leader 920 using the eyelet 924, as discussed further below.

The male suture guide 940 includes a base 946 that is received in and supported by the second end 990 of the guide tool arm 982, and a cylindrical stem 942 extending from an axial end of the base 946. The stem 942 is configured to releasably engage the leader eyelet 924. In particular, the stem 942 includes an axially extending opening 948 dimensioned to receive the eyelet 924 in a press fit manner. The stem 942 also includes a transverse opening 950 that extends through a diameter of the stem 942 in a direction transverse to the axial opening 948 and intersects the axial opening 948. Thus, when the eyelet 924 of the leader 920 is received within the axial opening 948 with a suture 1216 attached thereto, the suture 1216 passes freely along the transverse opening 950 without binding and a portion of the suture 1216 drapes outward from the transverse opening 950.

Referring to FIG. 7, detail B, the female suture guide 960 includes a base 968 that is received in and supported by the second end 990 of the guide tool arm 984, and a hollow cylindrical shell 962 extending from an axial end of the base 968. The shell 962 is configured to receive the leader 920 from the male suture guide 940, and to releasably retain the conical tip 922 therein. In particular, the shell 962 includes a first shell opening 966 through which the conical tip 922 of the leader 920 is inserted into the hollow interior of the shell 962, and a second shell opening 964 through which the leader 920 is withdrawn from the shell 962. The first shell opening 966 is located on an axial end of the shell 962, is generally circular in shape and has a dimension that is smaller than the dimension of the leader side 928. The second shell opening 964 is located on a sidewall of the shell 926, and has a shape that generally conforms to the size and shape of the tip 922 of the leader 920. In the illustrated embodiment, the second shell opening 964 includes a triangularly shaped portion through which the leader 920, including the conical tip 922, can be withdrawn from the shell 962.

In use, the suture leader is supported on a first arm 982 of the guide tool 980, and particular is retained in the axial opening 948 of the stem 942 of the male suture guide 940. The male suture guide 940 is configured to support the leader 920, and to transfer the leader 920 to the female suture guide 960 upon movement of the first arm 982 and the second arm 984 to the guide tool closed position. In the closed position, the male suture guide 940 and female suture guide 960 are touching or nearly touching. As a result, the leader 920, which is disposed on a side of the male suture guide 940 that faces the female suture guide 960, is pressed into the female suture guide 960. In particular, as the guide tool 980 moves to the closed position, the tip 922 is inserted, apex 926 first, into the first shell opening 966. Although the first shell opening 966 is small relative to the outer dimensions of the leader end 928, the shell 962 is formed to be relatively structurally weak so that the tip 922 of the leader 920 can pass through the first shell opening 966. Due to the size differences between the first shell opening 966 and the tip side 928, the leader 920 is prevented from being withdrawn from the shell 962 through the first opening 966. The leader 920, housed within the shell 962 of the female suture guide 960, is now retained on the second end 990 of the second arm 984 of the guide tool 980, and moves with the second arm 984 when the guide tool 980 is opened. Thus, by using the guide tool 980, a suture 1216 can be secured to the first arm 982 by attaching a leader 920 to the male suture guide 940, and the suture 1216 can then passed to the second arm 984 via the female suture guide 960 through a simple operation of the guide tool 980. Since the guide tool arms 982, 984 are configured to fit within the pedicle screw heads 302, and because the pedicle screw heads 302 each include axially-elongated side openings 310, 312, a suture 1216 can be passed subcutaneously and submuscularly between adjacent pedicle screws 300 after implantation of the pedicle screws 300 in the spine. This feature is important to the method of using the system 20, as discussed further below.

Referring to FIGS. 8(a)-8(e), some examples of alternative embodiment male suture guides 1340 are illustrated. For example, in FIG. 8(a), the male suture guide 1340a may be formed integrally with the suture leader, and includes a base 1346a that is configured to be supported on the second end of the guide tool arm 982, the base 1346a including an opening 1342a to which a suture can be secured. The male suture guide 1340a also includes a conical tip 1322a to facilitate insertion into the corresponding opening of the female suture guide 960. FIGS. 8(b) to 8(e) illustrate additional alternative embodiments of the male suture guide, where like reference numbers refer to like structures. In these alternative embodiments, it can be seen that the base 1346 can be formed having a larger outer diameter than the tip 1322 (FIG. 8(b)) or formed having a non-cylindrical shape (FIGS. 8(b), 8(d), 8(e)). In addition, the tip 1322 is not limited to having a conical shape (FIGS. 8(b), 8(c), 8(d)).

Referring to FIGS. 9(a)-9(d), examples of alternative embodiment female suture guides 1360 are illustrated. For example, in FIG. 9(a), the female suture guide 1360a includes a base 1362a that is configured to be supported on the second end of the guide tool arm 984. In this example, the base 1362a also serves as the shell portion and includes a first shell opening 1366a through which the leader tip 922, 1322 is inserted into the hollow interior of the base 1362a, and a second shell opening 1364a through which the leader 920 is withdrawn from the base 1362a. FIGS. 9(b) to 9(d) illustrate additional alternative embodiments of the female suture guide 1360, where like reference numbers refer to like structures. In these alternative embodiments, it can be seen that the first shell opening 1366 and second shell opening 1364 may be formed having different shapes (FIGS. 9(b), 9(c), 9(d)), for example to compliment a corresponding structure of the male suture guide and/or facilitate insertion and/or extraction of the leader from the female suture guide 1360.

Figures 10, 11:
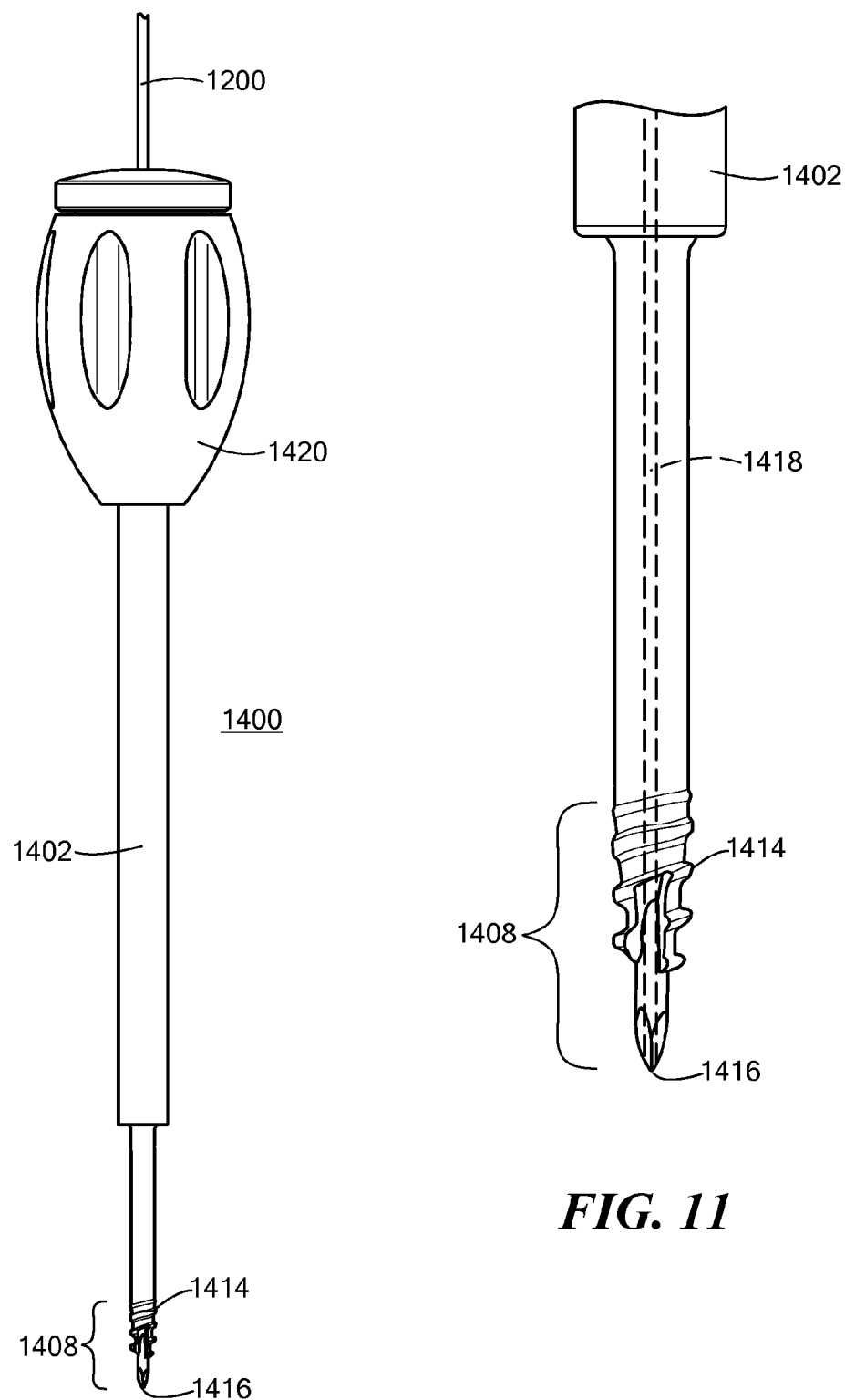
FIG. 10 is a side view of an awl used during implantation of the spinal fixation system of FIG. 2.
FIG. 11 is a detail view of the tip of the awl of FIG. 10.

Referring to FIGS. 10 and 11, an awl 1400 is used to prepare each vertebra for implantation, as described further below. The awl 1400 includes an elongated shaft 1402 that terminates at one end in a handle 1420 and at the other end with a cutting tip 1408. The cutting tip 1408 has a drill portion 1416 on a leading end thereof, and a tap portion 1414 disposed between the drill portion 1416 and the shank 1402. In addition, an axially extending through hole 1418 that extends from the handle 1420 to the cutting tip 1408 is dimensioned to receive a Kirshner pin 1200.

Referring to FIGS. 12-39, an example of a minimally invasive method for achieving spinal stabilization using spinal fixation system 20 will now be described.

In Step 1, a pedicle screw 300 is implanted into each vertebra 4 of a portion of the spine 2 to be stabilized (FIGS. 12-20). Implantation of pedicle screws 300 includes the following:

Step 1*a*. Provide an incision through the skin 10 overlying the vertebra 4. In general, the incision length corresponds to the outer diameter of the pedicle screw 300, and may be slightly less due to the pliability of skin. In the illustrated embodiment, the pedicle screw 300 is approximately 1 cm in diameter, whereby an incision of at most 1 cm is required to accommodate pedicle screw 300.

Figure 12:
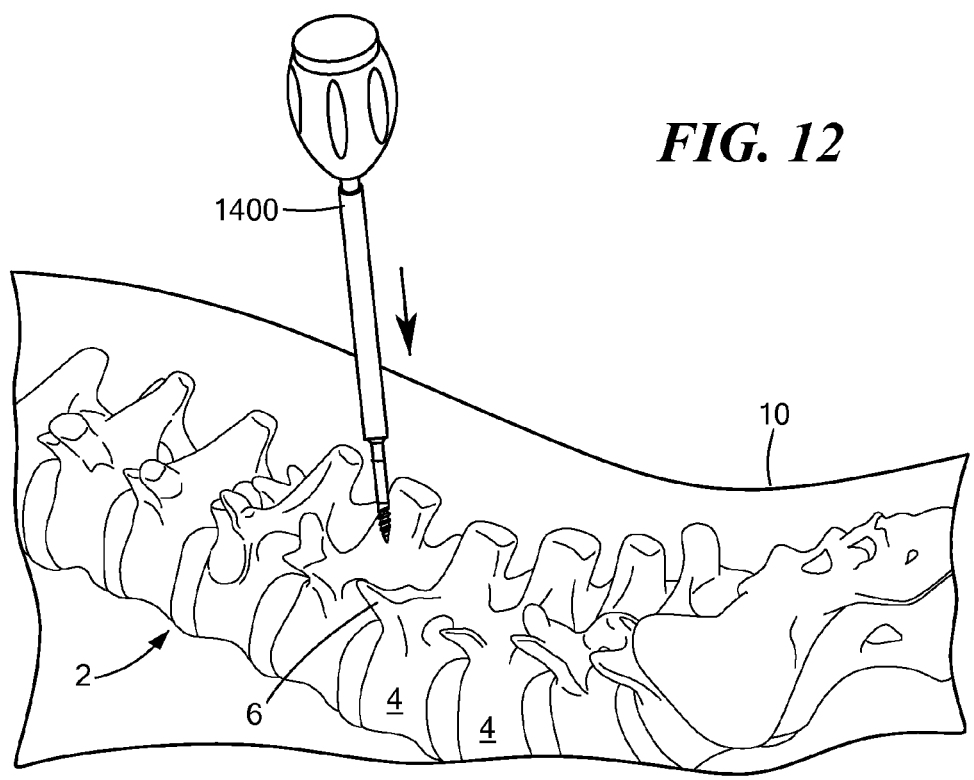
FIGS. 12-14 illustrate use of the awl to form a pedicle screw hole and facilitate insertion of a Kirshner pin into a vertebra.

Step 1*b*. Referring to FIG. 12, prepare the vertebra 4 to receive the pedicle screw 300 by forming a threaded hole in the pedicle 6. An awl 1400 (described in co-pending U.S. applications having Ser. Nos. 13/161,705 and 13/161,698 and incorporated by reference herein) is inserted into the incision and is used to locate the pedicle and form the threaded hole therein. Correct positioning is verified using an imaging device such as a C-arm or fluoroscope.

Figure 13:
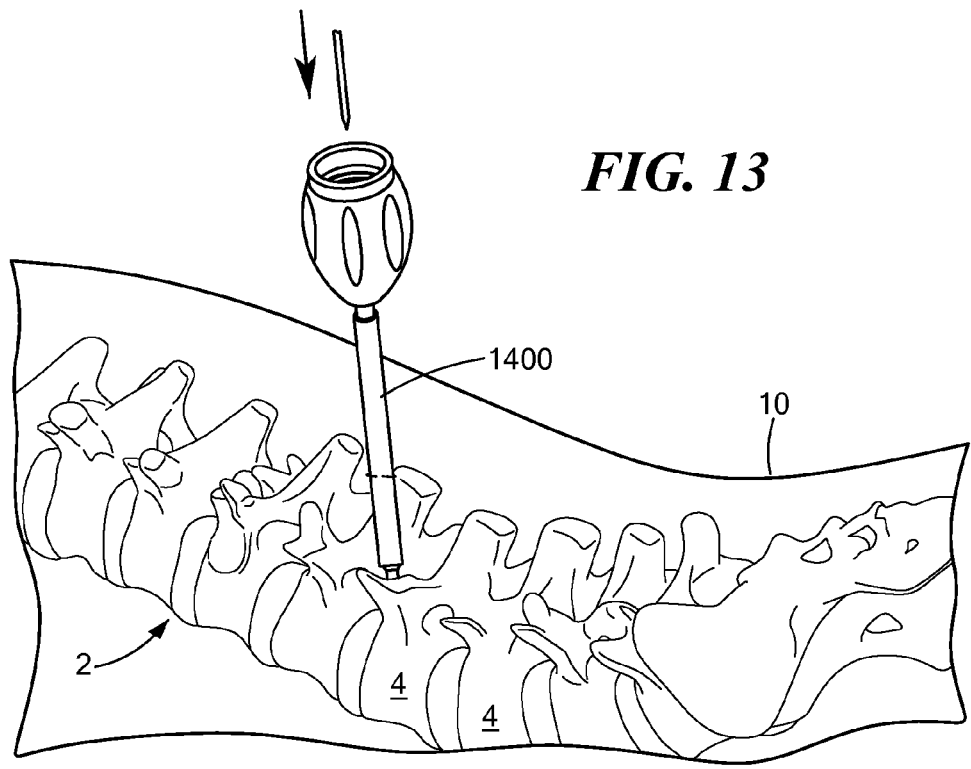

Step 1*c*. Referring to FIG. 13, insert a Kirshner pin 1200 through the axial passageway 1418 of the awl and into the vertebra 4 at the desired implantation location.

Figure 14:
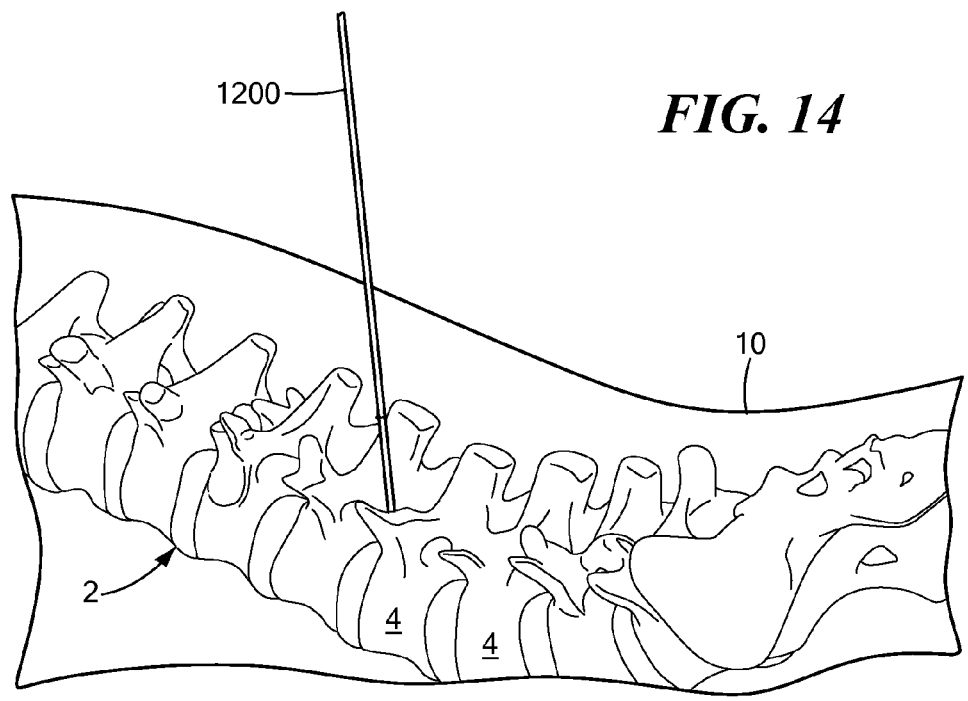

Step 1*d*. Referring to FIG. 14, removal the awl 1400, leaving the pin 1200 in place.

Figure 15:
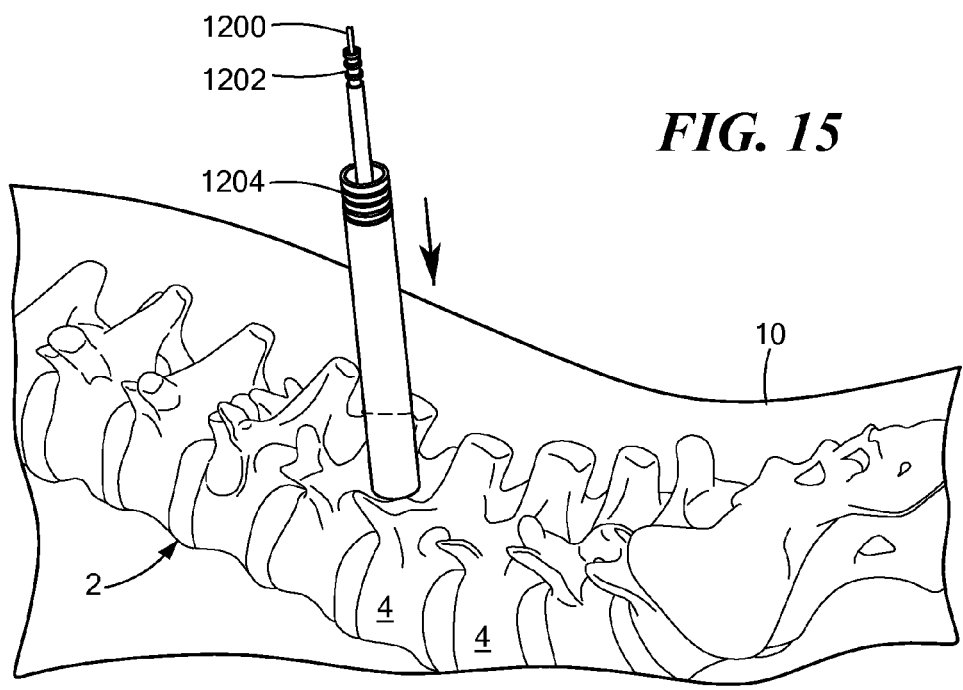
FIG. 15 illustrates dilation of soft tissues in the vicinity of the Kirshner pin.
Figure 16:
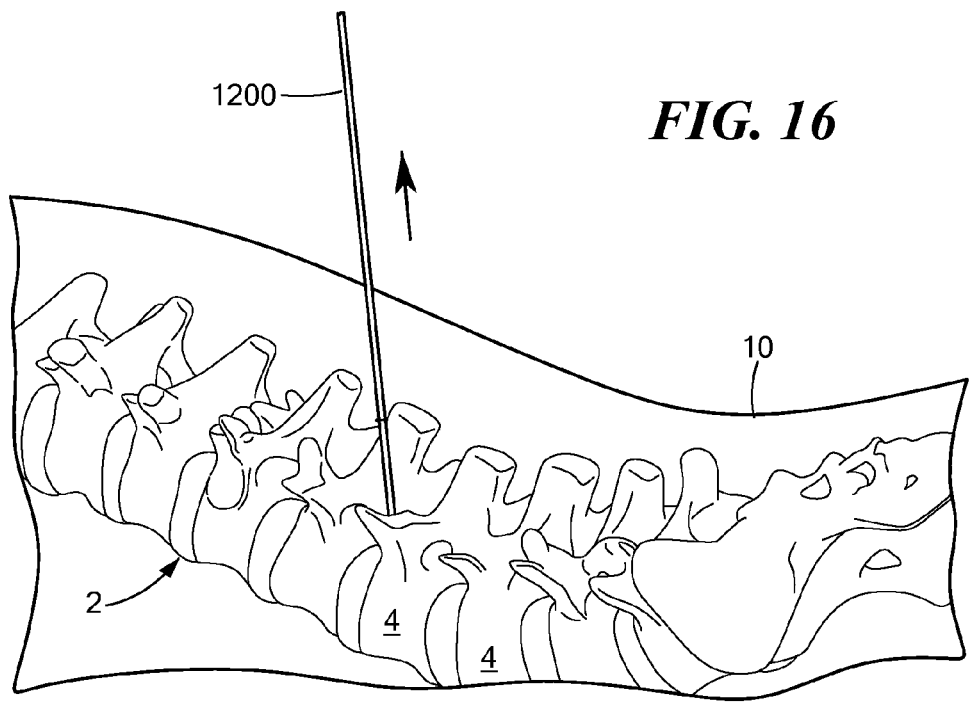
FIG. 16 illustrates that the Kirshner pin remains in place after completion of dilation and removal of the dilation tubes.

Step 1*e*. Referring to FIGS. 15-16, insert a series of dilation cannulas 1202, 1204 into the incision over the pin 1200, starting with a relatively small-diameter cannula 1202, and each successive cannula having a slightly larger outer diameter. Although only two cannulas 1202, 1204 are shown, six to eight cannulas may be used in order to dilate the skin 10, muscle and other soft tissues in the vicinity of the pin 1200 and create space for insertion of the pedicle screw 300 into the body (FIG. 15). The pin 1200 is used to stabilize and direct each respective dilation cannula 1202, 1204 during dilation. After dilation is completed, the dilation cannulas 1202, 1204 are withdrawn, leaving the pin 1200 in place (FIG. 16).

Figure 17:
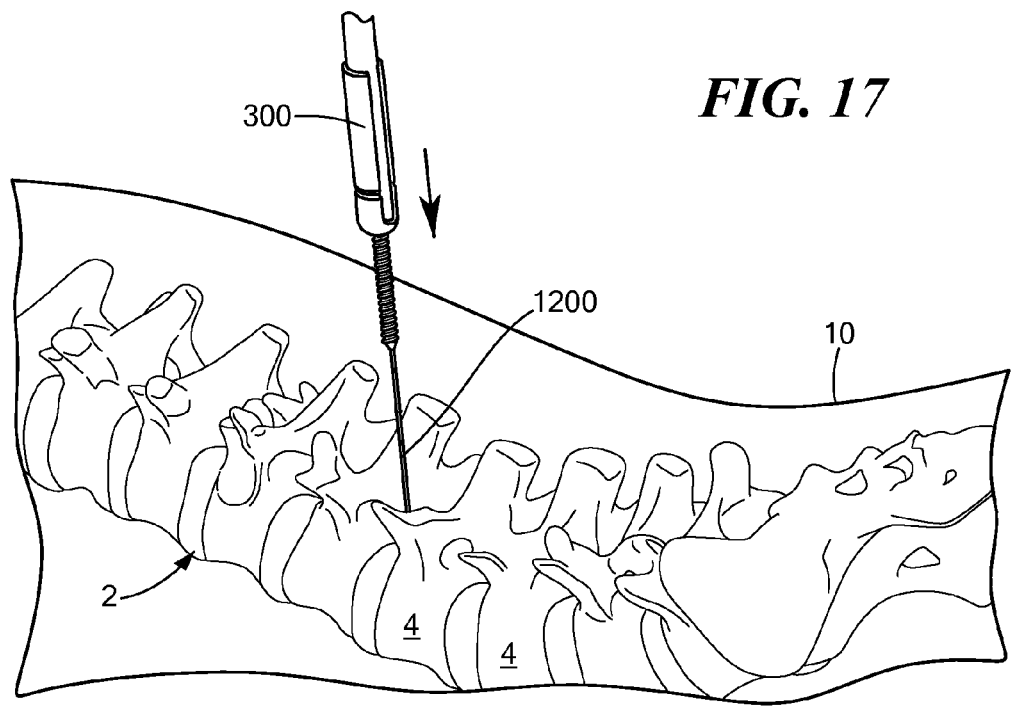
FIG. 17 illustrates insertion of the pedicle screw into the body over the Kirshner pin.
Figure 18:
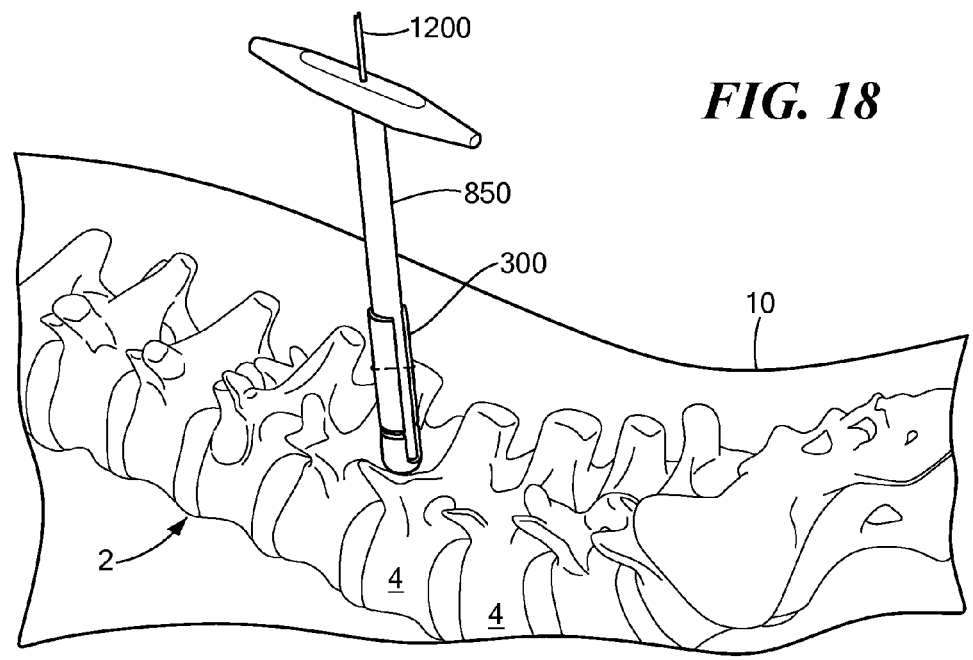
FIGS. 18-19 illustrate implantation of the pedicle screw in the vertebra.

Step 1*f*. Referring to FIGS. 17-18, implant the pedicle screw 300 in the pre-threaded drill hole of the vertebra 4 by passing it along the pin 1200. Specifically, the pedicle screw 300 is loaded onto the pin 1200 so that the pin 1200 is received within the shank axial through hole 350 and the interior space of the pedicle screw head 302. The pin 1200 serves to stabilize and direct the pedicle screw shank 344 so that the threads 348 on the shank 344 engage with and are screwed onto the drill hole threads. In the illustrated embodiment, a driving tool is used to rotate the pedicle screw 300, screwing the pedicle screw into the hole in the vertebra 4. As seen in the figure, when the shank 344 is fully screwed into the vertebra 4, a portion of pedicle screw head 302 protrudes through the incision outwardly relative to the skin 10.

Figure 19:
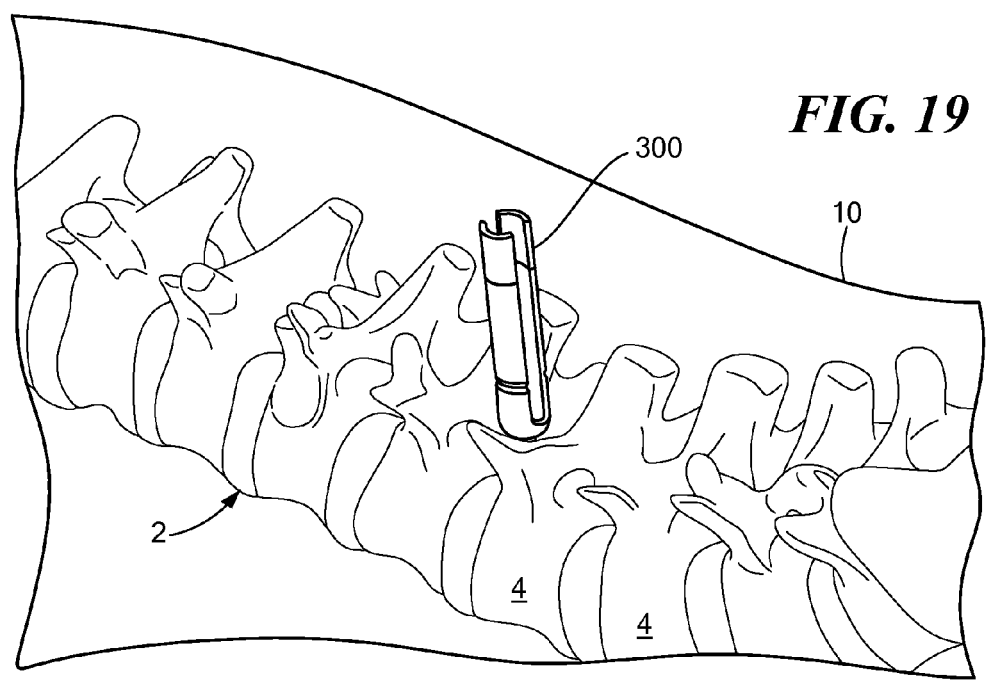

Step 1*g*. Referring to FIG. 19, remove driving tool and pin 1200 from the incision, leaving the pedicle screw 300 in place.

Figure 20:
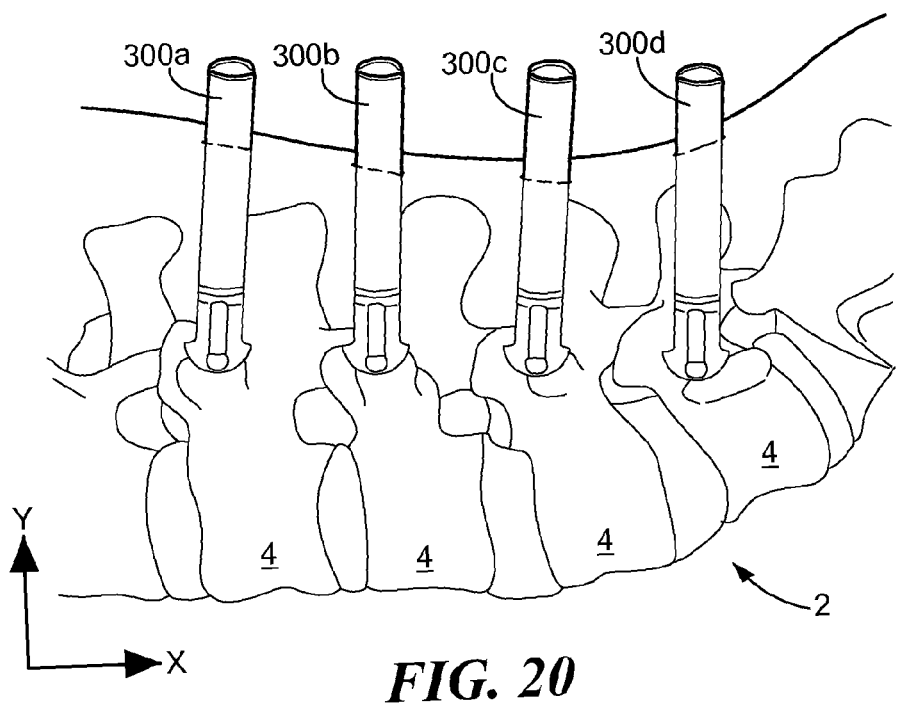
FIG. 20 illustrates repeating the pedicle screw implantation steps for several adjacent vertebrae.

Step 1*h*. Referring to FIG. 20, repeat the previous pedicle screw 300 implantation steps 1*a*-1*g* for each vertebra 4 to be stabilized. In the illustrated embodiment, four vertebrae 4 are to be stabilized, whereby a pedicle screw 300 is implanted in each of the four vertebrae 4 (300*a*, 300*b*, 300*c*, 300*d*).

Figure 21:
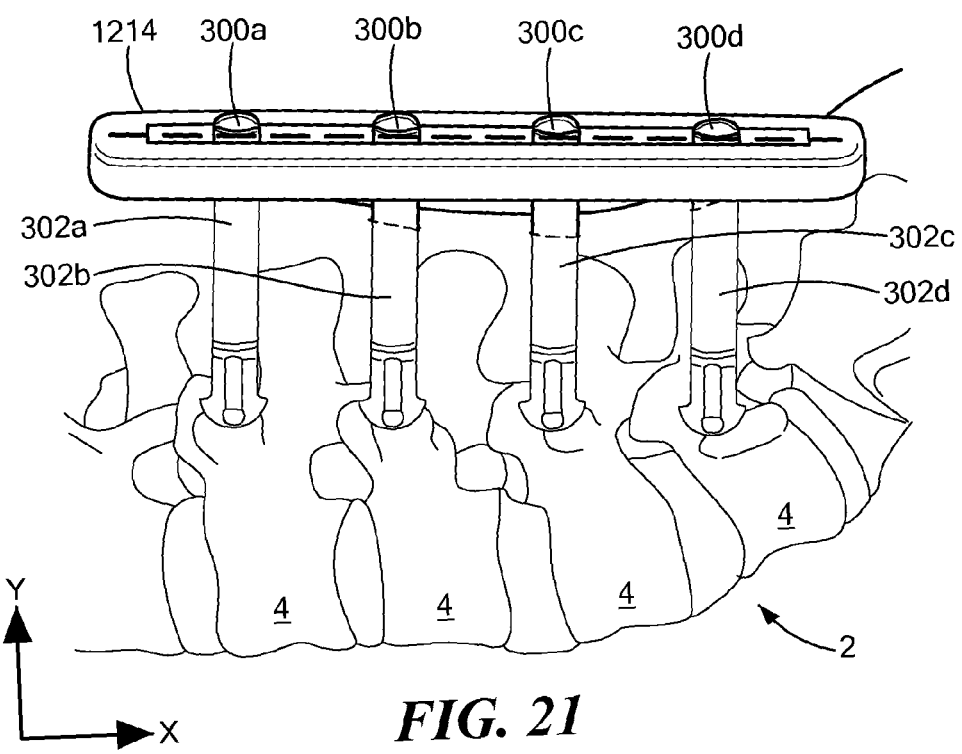
FIG. 21 illustrates using a device to align the pedicle screw heads.

Referring to FIG. 21, Step 2 includes aligning the respective pedicle screw heads 302 using an alignment tool 1214 so that the longitudinal axes of the screws 300 are parallel to each other and vertically aligned. In FIG. 21, a reference frame is defined in which an x axis corresponds generally to a longitudinal axis of the spine 2 and is oriented horizontally, and a y axis transverse to the x axis is oriented vertically and corresponds to an anterior-posterior direction of the spine 2.

In step 2, the respective pedicle screw heads 302 are aligned so that the first and second pedicle screw openings 310, 312 open along the x axis, and thus the respective pedicle screw transverse openings 318 are aligned with the x axis.

Figure 23:
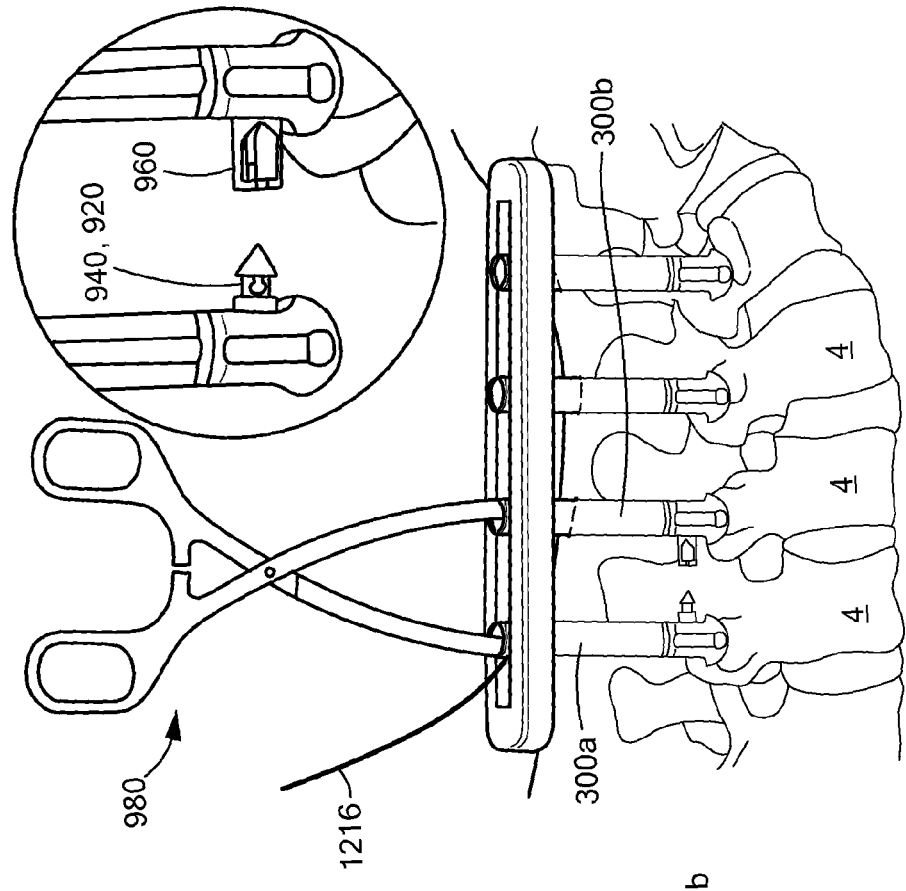
FIGS. 22-29 illustrate using the guide tool assembly to thread a suture subcutaneously and submuscularly between respective first ends of the implanted pedicle screw heads.
Figure 22:
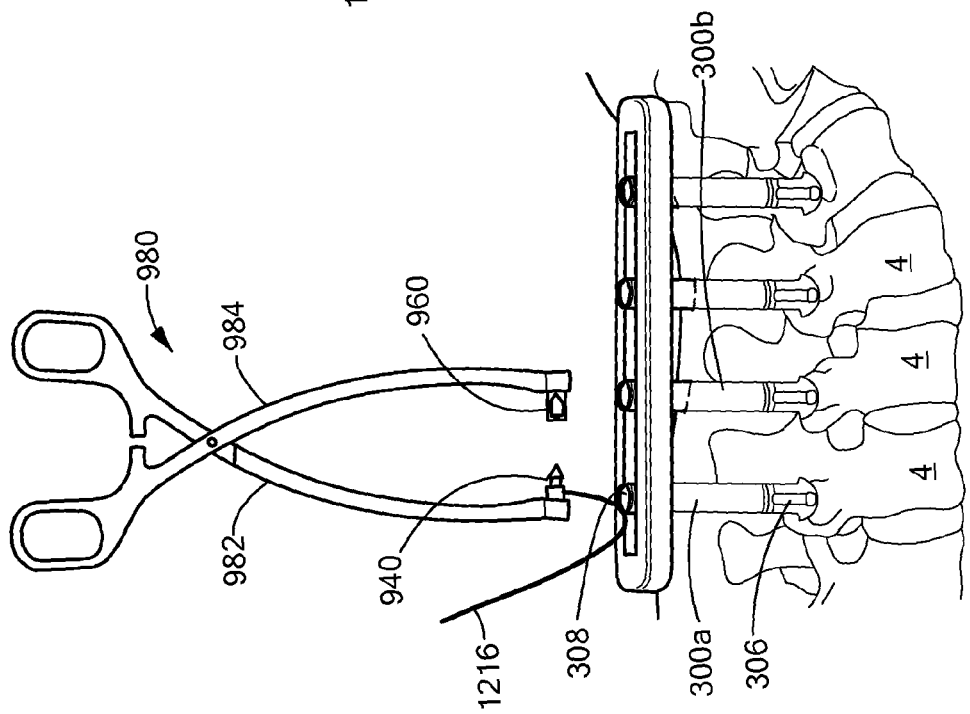

Step 3 includes linking the pedicles screws 300 by subcutaneously threading a suture 1216 through the respective pedicle screw heads 302. Linking the pedicle screws 300 includes the following:

Step 3*a*. Referring to FIGS. 22-23, use the suture guide tool 980 to insert a suture 1216 into the cranial-most pedicle screw 300*a* such that the suture leading end passes through the interior space of the pedicel screw head 302 from the second end 308 of the head to the first end 306 (e.g., along the y axis).

Figure 25:
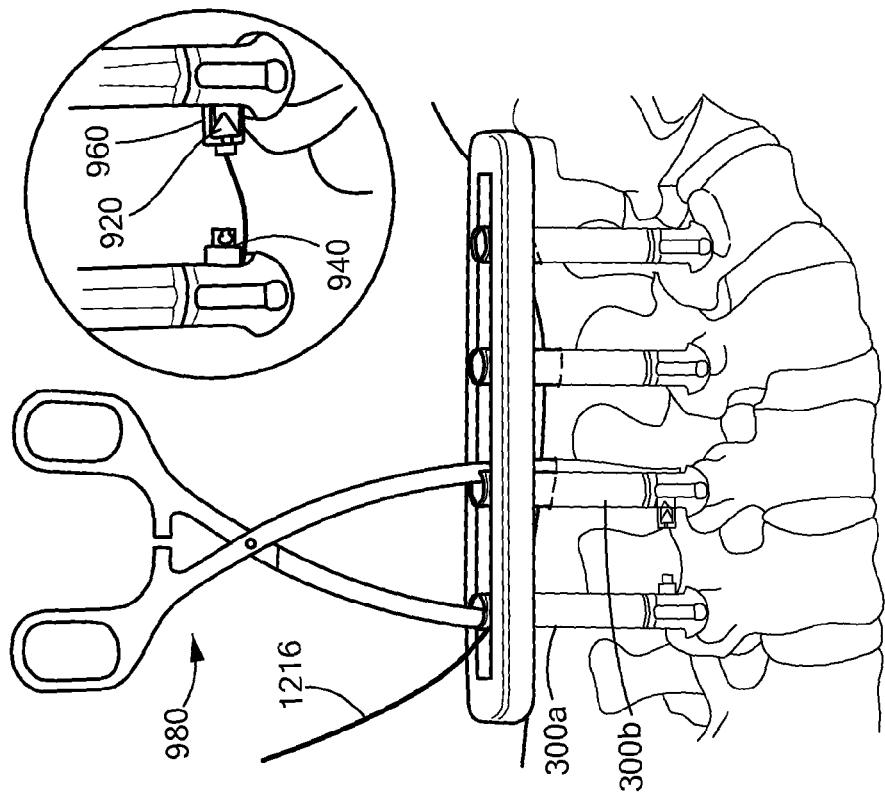
Figure 24:
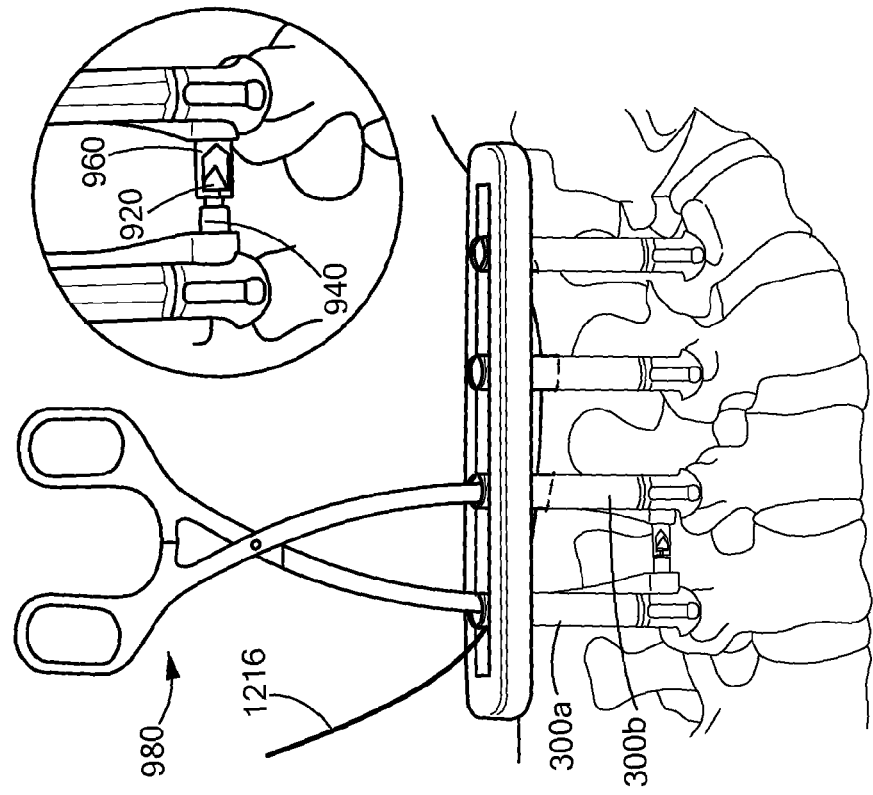

Step 3*b*. Referring to FIGS. 24-25, actuate the guide tool 980 to guide the suture 1216 from the first end 306 of the cranial-most pedicle screw 300*a* to the first end 306 of the adjacent pedicle screw 300*b* along the x axis and generally parallel to the longitudinal axis of the spine 2. In particular, the suture 1216 is transferred between adjacent pedicle screws 300*a*, 300*b* by actuating the guide tool 980 from an open position to a closed position, whereby the leader 920 is transferred from the male suture guide 940 to the female suture guide 960 (FIG. 24). The suture 1216 is then moved to the adjacent pedicle screw 300*b* by actuating the suture guide to an open position (FIG. 25).

Figure 26:
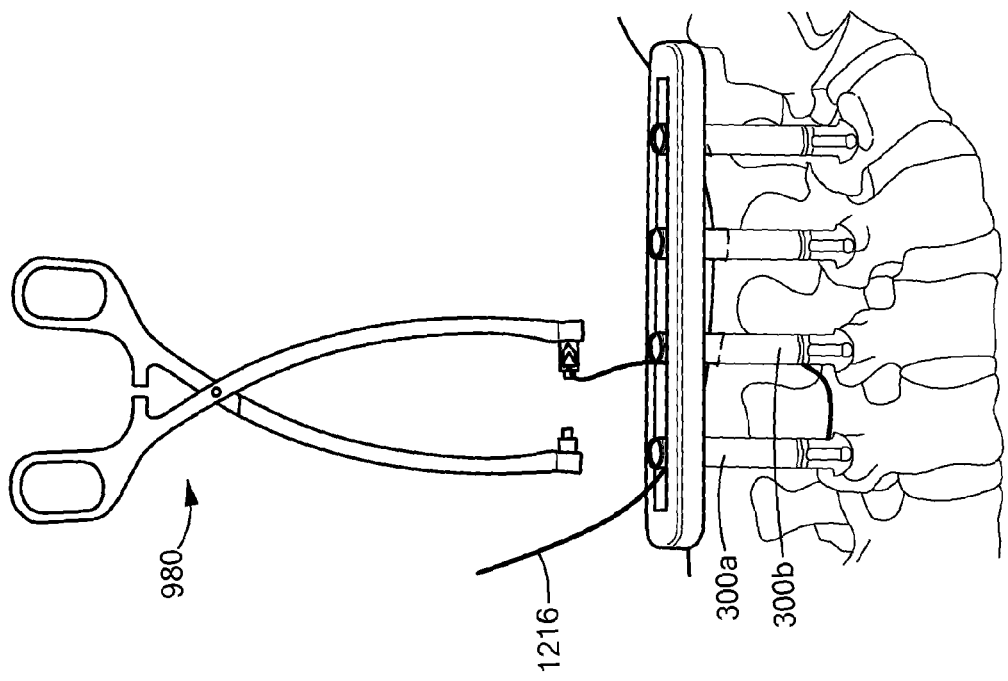

Step 3*c*. Referring to FIG. 26, the suture guide tool 980 is withdrawn from the pedicle screw heads 302*a*, 302*b*, with the suture 1216 now linking the cranial-most pedicle screw 300*a* and the adjacent pedicle screw 302*b*. At this time, the leader 920 is transferred back to the male suture guide 940, in preparation for repeating steps 3*a* and 3*b* for pedicle screws 300*b* and 300*c*.

Figure 27:
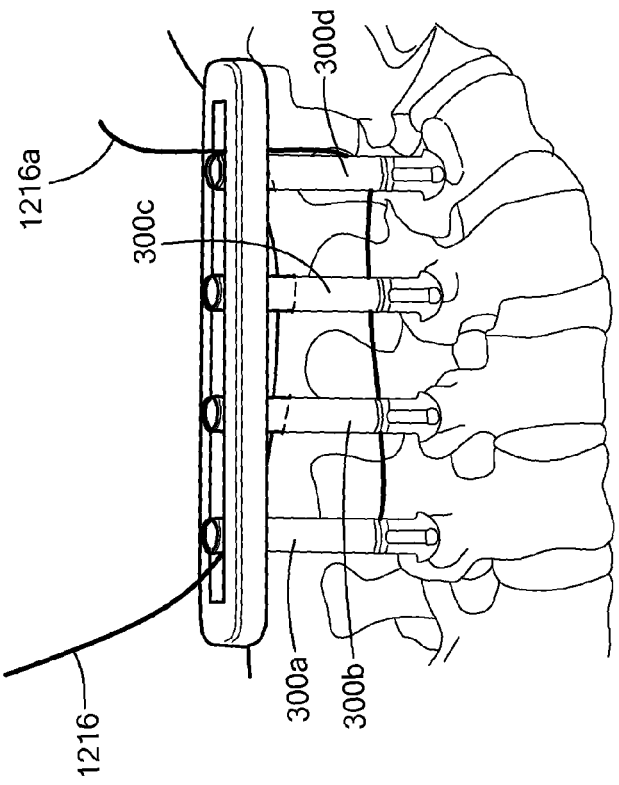

Step 3*d*. Referring to FIG. 27, Steps 3*a*-*c* are repeated until the first end 306 of each pedicle screw 300*a*, 300*b*, 300*c*, 300*d* is serially linked subcutaneously and submuscularly via the suture 1216. Although the linking step is described as proceeding from the cranial-most pedicle screw 300*a* to the caudal-most pedicle screw 300*d*, the method is not limited to this. For example, the method can include proceeding from caudal-most to cranial-most pedicle screw 300.

Figures 28, 29:
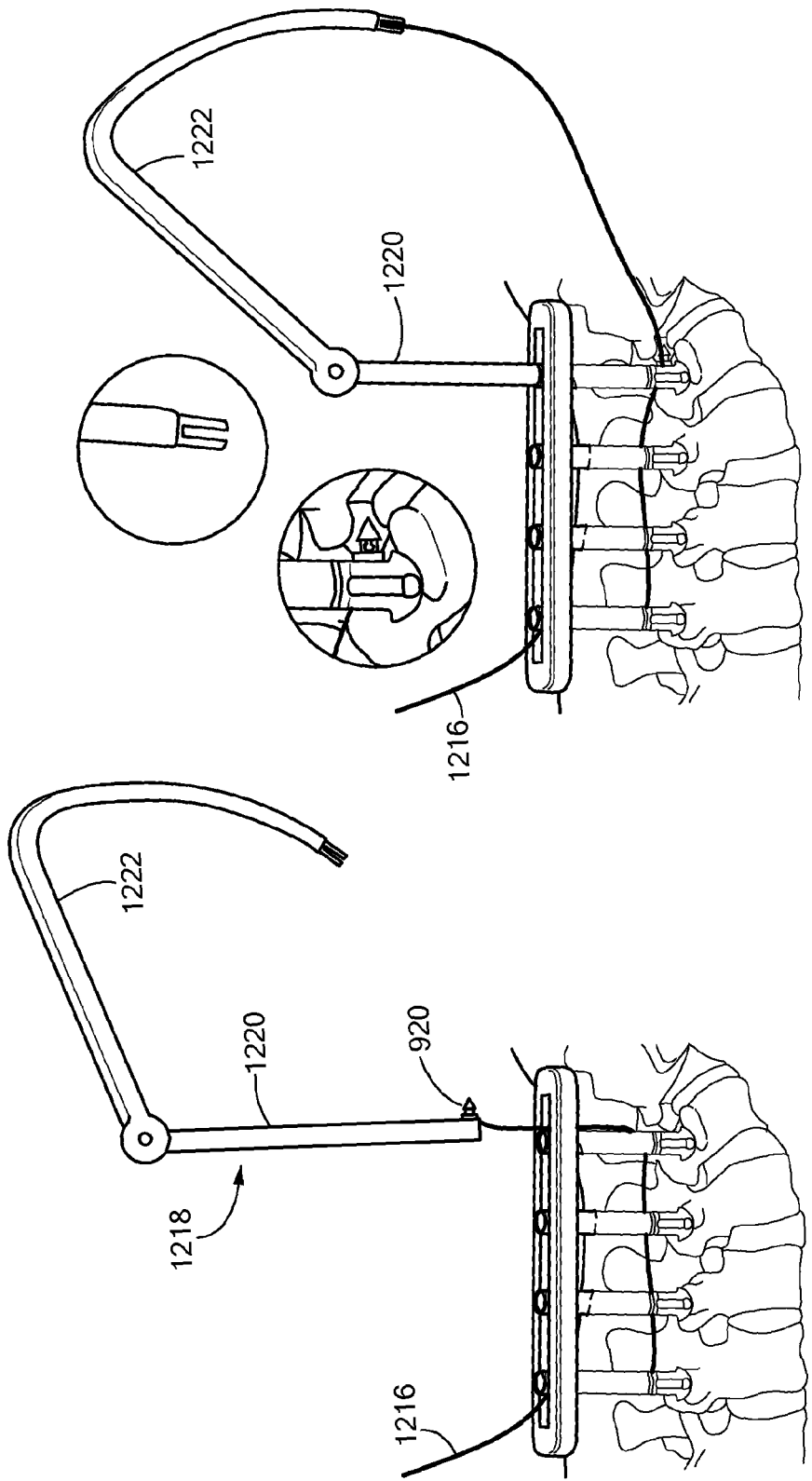

Step 4 includes withdrawing the suture leading end 1216*a* from the body through a small access incision (1 cm or less) located caudally with respect to the caudal-most pedicle screw 300*d*. Withdrawing the suture includes the following:

Step 4*a*. Referring to FIGS. 28-29, a compass tool 1218 is provided that facilitates withdrawal of the suture 1216 from the body. The compass tool 1218 includes a base leg 1220 configured to hold the suture leader 920 and a curved pivoting leg 1222 configured to receive the suture leader 920, and to pivot relative to the base leg 1220 about a pivot axis at one end of the base leg 1220. As seen in FIG. 28, the base leg 1220 holds the suture leader 920 adjacent the pedicle screw 300*d*. In subsequent actions, the base leg 1220 is inserted into the caudal-most pedicle screw 300*d*, and the pivoting leg 1222 is rotated (clockwise in the figure) relative to the base leg 1220 so as to pass through the access incision. As a result, the suture leader 920 is moved from an end of the base leg 1220 to an end of the pivoting leg 1222 in a manner similar to that used within the suture guide assembly 900. The pivoting leg 1222 is then rotated (counterclockwise in the figure) relative to the base leg 1220 to withdraw the suture 1200 from the access incision (FIG. 29).

Referring to FIGS. 30 and 31, Step 5 includes providing a pedicle rod 200. In particular, the pedicle rod 200 must be provided in a length that is at least sufficient for the rod to simultaneously span all implanted pedicle screws 300*a*-300*d*. In some embodiments, the respective protruding second ends 308 of the pedicle screws 300 may be used as a template to cut a length of rod stock to the desired length (FIG. 30). In addition, the pedicle rod 200 is preformed to have a curvature (shown as a dashed line) corresponding to the curvature of the spine 2. In particular, the curvature of the pedicle rod 200 is adjusted ex vivo and prior to insertion into the body by bending the rod 200 to correspond to the curvature of a line defined by the upper surfaces of the second ends 308 of the implanted pedicle screws 300 (FIG. 31).

Figure 32:
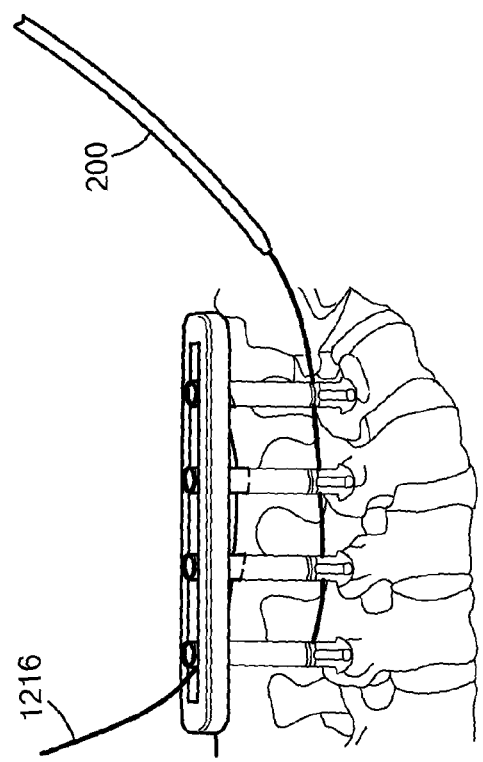
FIG. 32 illustrates threading the pedicle rod over the suture and across the respective implanted pedicle screw heads.

Referring to FIG. 32, Step 6 includes subcutaneously and submuscularly threading the sized- and shaped-pedicle rod 200 onto the suture 1216 by passing the suture 1216 through hollow interior passageway 210 of the pedicle rod 200.

Step 7 includes passing the pedicle rod 200 along the suture 1216 into the body and through each respective pedicle screw head 302 such that the pedicle rod 200 resides in the transverse passage 316 adjacent the first end 306 of each respective pedicle screw head 302.

Step 8 includes removing the suture 1216 from the body, leaving the pedicle rod 200 in position within the series of pedicle screws 300.

Figure 33:
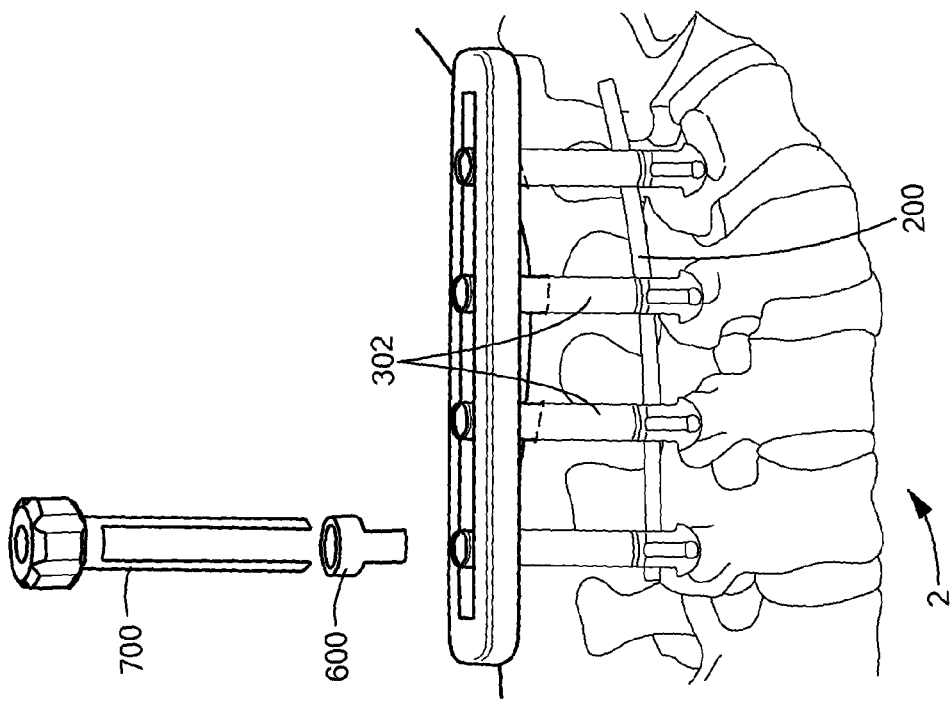
FIG. 33 illustrates assembling a cap and stabilizer on the pedicle screw head.

Step 9 includes securing the pedicle rod 200 to each pedicle screw 300. The following steps are used to secure the pedicle rod 200 to a pedicle screw:

Step 9*a*. Referring to FIG. 33, stabilize the pedicle rod 200 with respect to the pedicle screw 300 by securing the cap 600 to the pedicle screw head second end 308, and then inserting the stabilizer tool 700 through the cap and onto the pedicle screw head 302. When assembled, the stabilizer tool legs 712 securely seat the pedicle screw rod 200 within the interior space of the pedicle screw head 302 at the lowermost aspect of the first and second openings 310, 312, and maintain the rod 200 in that position during the subsequent step (9*b*).

Figure 34:
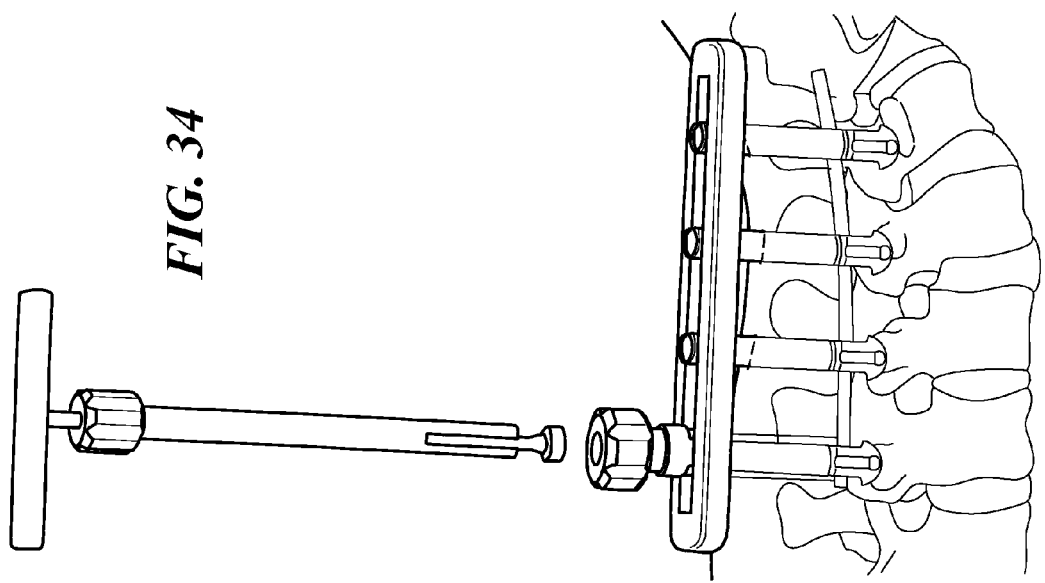
FIG. 34 illustrates insertion of a fastener through the cap and stabilizer to secure the pedicle rod to the pedicle screw.

Step 9*b*. Referring to FIG. 34, secure the pedicle rod 200 relative to the pedicle screw 300 by using the actuator 850 to drive the set screw 500 into the pedicle screw head 302 such that the exterior threads 508 of the set screw 500 engage with corresponding threads 326 provided on the interior surface of the first end 306 of the pedicle screw head 302. As a result, the pedicle rod 200 is retained between the set screw 500 and first end 306 of the pedicle screw 300.

Figure 35:
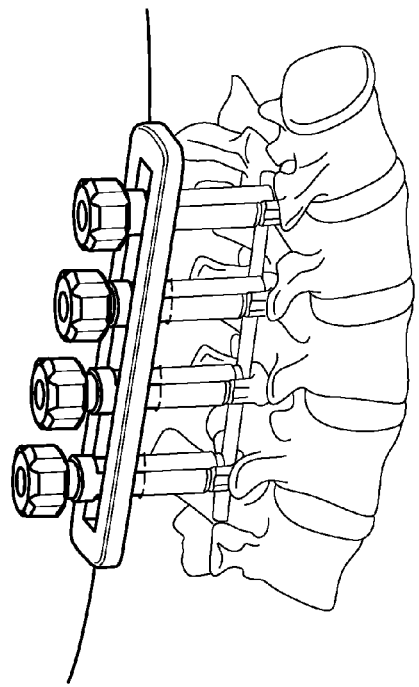
FIG. 35 illustrates repeating the step shown in FIG. 34 for each pedicle screw.

Step 9*c*. Referring to FIG. 35, repeat steps 9*a* and 9*b* until the pedicle rod 200 is secured to each pedicle screw 300*a*-300*d*.

Figure 36:
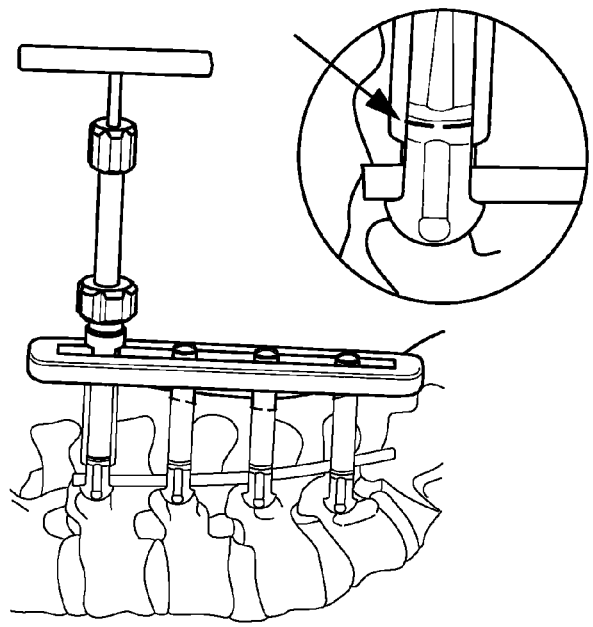
FIGS. 36-37 illustrate using the breaking tool to break off a dorsal portion of each pedicle screw head.
Figure 37:
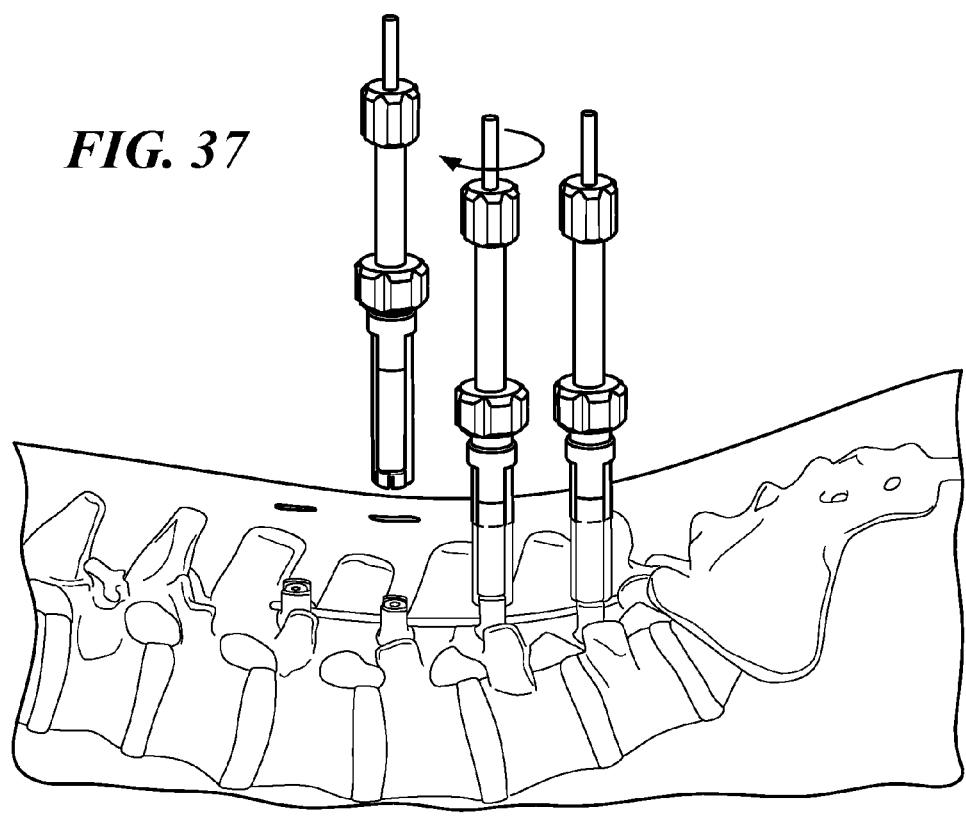
Figure 38:
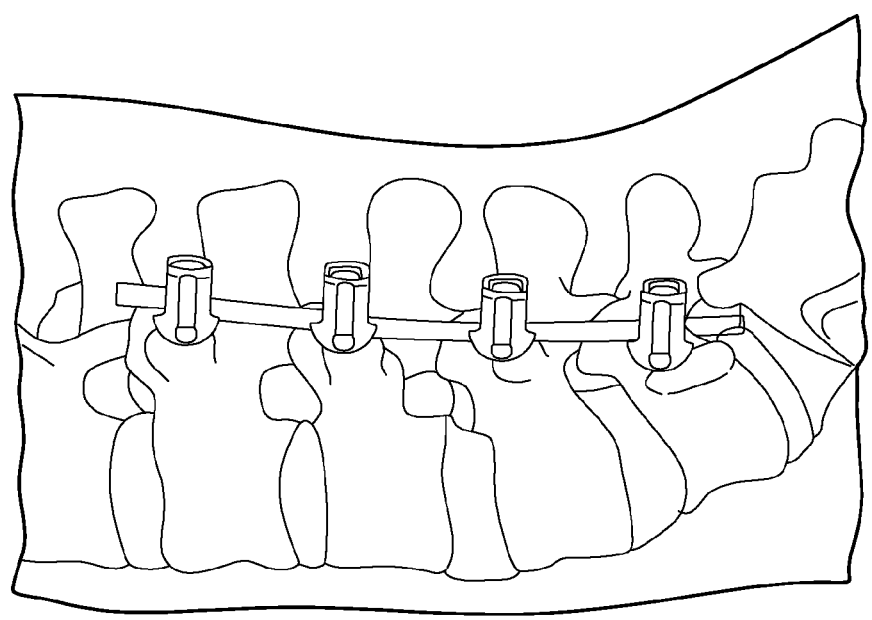
FIG. 38 illustrates the implanted spinal fixation system.

Step 10 includes removing the pedicle screw head dorsal portion 324 from the remainder of the head 302 of each pedicle screw. The removing step includes the following:

Step 10*a*. Referring to FIGS. 36-38, apply a twisting force to the dorsal portion 324 using the breaking tool 800 such that the dorsal portion 324 breaks away from the first end of the pedicle screw along the annular breakway region 318, and withdrawing the separated dorsal portion 324 from the body.

Step 11 includes closure of all minimal incisions.

A selected illustrative embodiment of the invention is described above in some detail. It should be understood that only structures considered necessary for clarifying the present invention have been described herein. Other conventional structures, and those of ancillary and auxiliary components of the system, are assumed to be known and understood by those skilled in the art. Moreover, while a working example of the present invention has been described above, the present invention is not limited to the working example described above, but various design alterations may be carried out without departing from the present invention as set forth in the claims.

What is claimed is:

1. A suture guide assembly including
   a suture leader having a conical tip and an eyelet protruding from the conical tip, the eyelet having an opening transverse to a longitudinal axis of the conical tip and configured to retain a suture, and
   a guide tool including pivotably-joined first and second arms, the first arm terminating at a first end in a male suture guide, the second arm terminating at a first end in a female suture guide,
   wherein the male and female suture guides are configured to permit the suture leader to be passed from the male suture guide to the female suture guide upon movement of the first and second arms between an open position in which the male and female suture guides are spaced apart at least a distance between two adjacent vertebrae and a closed position in which the male and female suture guides are adjacent.

2. The suture guide assembly of claim 1, wherein the male suture guide includes a cylindrical stem configured to releasably engage the suture leader eye, and the female suture guide includes a cylindrical shell configured to releasably engage the suture leader conical tip, and
   the guide tool is configured so as to support the male and female suture guides so that the conical tip is at least partially received within the shell when the guide tool is in the closed position.

3. The suture guide assembly of claim 2 wherein the shell includes a first shell opening through which the suture leader is inserted into the shell, and a second shell opening through which the suture leader is withdrawn from the shell.

4. The suture guide assembly of claim 3 wherein the second shell opening has a shape that generally conforms to the shape of the suture leader.

5. The suture guide assembly of claim 3 wherein the first shell opening has a dimension that is smaller than the dimension of the widest portion of the suture leader.

6. The suture guide assembly of claim 5 wherein the first shell opening is configured such that when the guide tool is moved from the open position to the closed position, the conical tip of the suture leader is driven through the first shell opening, and is prevented from being retracted from the shell via the first shell opening.

7. The suture guide assembly of claim 1, wherein the first and second arms are angled.

8. The suture guide assembly of claim 7, wherein the angle is between 90-180 degrees.

* * * * *